United States Patent
Rossi et al.

(10) Patent No.: US 10,272,165 B2
(45) Date of Patent: *Apr. 30, 2019

(54) APTAMER-MRNA CONJUGATES FOR TARGETED PROTEIN OR PEPTIDE EXPRESSION AND METHODS FOR THEIR USE

(71) Applicant: CITY OF HOPE, Duarte, CA (US)

(72) Inventors: John J. Rossi, Alta Loma, CA (US); Maggie Bobbin, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,280

(22) Filed: Jul. 11, 2016

(65) Prior Publication Data

US 2017/0043040 A1 Feb. 16, 2017

Related U.S. Application Data

(62) Division of application No. 14/541,639, filed on Nov. 14, 2014, now Pat. No. 9,388,418, which is a division of application No. 13/494,880, filed on Jun. 12, 2012, now Pat. No. 8,916,696.

(60) Provisional application No. 61/496,027, filed on Jun. 12, 2011.

(51) Int. Cl.
| | |
|---|---|
| *C07H 21/04* | (2006.01) |
| *A61K 49/12* | (2006.01) |
| *C12N 15/11* | (2006.01) |
| *C12N 15/113* | (2010.01) |
| *C12N 15/115* | (2010.01) |
| *A61K 38/46* | (2006.01) |
| *A61K 49/00* | (2006.01) |
| *A61K 47/54* | (2017.01) |
| *A61K 48/00* | (2006.01) |

(52) U.S. Cl.
CPC ............ *A61K 49/12* (2013.01); *A61K 38/465* (2013.01); *A61K 47/549* (2017.08); *A61K 49/0054* (2013.01); *C12N 15/111* (2013.01); *C12N 15/115* (2013.01); *C12N 15/1132* (2013.01); *A61K 48/00* (2013.01); *C12N 2310/14* (2013.01); *C12N 2310/16* (2013.01); *C12N 2310/3519* (2013.01); *C12N 2320/32* (2013.01); *C12Y 301/21004* (2013.01)

(58) Field of Classification Search
CPC ..................................................... A61K 48/00
See application file for complete search history.

(56) References Cited

U.S. PATENT DOCUMENTS

| | | | |
|---|---|---|---|
| 5,977,089 A | 11/1999 | Arimilli | |
| 6,005,087 A | 12/1999 | Cook | |
| 6,031,086 A | 2/2000 | Switzer | |
| 6,127,533 A | 10/2000 | Cook | |
| 6,225,460 B1 | 5/2001 | Bischofberger | |
| 6,399,754 B1 | 6/2002 | Cook | |
| 6,403,779 B1 | 6/2002 | Kawasaki | |
| 7,794,931 B2 | 9/2010 | Breaker | |
| 2004/0067503 A1 | 4/2004 | Tan | |
| 2005/0260164 A1 | 11/2005 | Jolly et al. | |
| 2011/0052697 A1 | 3/2011 | Farokhzad et al. | |

FOREIGN PATENT DOCUMENTS

WO 2011/130458 10/2011

OTHER PUBLICATIONS

Berges, B.K., et al., HIV-1 infection and CD4 T cell depletion in the humanized Rag2-I-gamma c-I(RAG-hu) mouse model. Retrovirology, 2006.3: p. 76.
Berges, B.K., et al., Mucosal transmission of R5 and X4 tropic HIV-I via vaginal and rectal routes in humanized Rag2-1-gammac-1-(RAG-hu) mice. Virology, 2008. 373(2): p. 342-51.
Berges, B.K., et al., Humanized Rag2(-I-)gammac(-I-) (RAG-hu) mice can sustain long-term chronic HIV-I infection lasting more than a year. Virology, 2010. 397(1): p. 100-3.
Chu, T.C., et al., Aptamer:toxin conjugates that specifically target prostate tumor cells, Cancer Res, 2006. 66(12): p. 5989-92.
Denton, P.W. and IV. Garcia, Novel humanized murine models for HIV research. Curr HIV/AIDS Rep, 2009.6(1): p. 13-9.
Ellington, A.D. and J. W. Szostak, In vitro selection of RNA molecules that bind specific ligands. Nature, 1990.346(6287): p. 818-22.
Holt, N., et al., Human hematopoietic stem/progenitor cells modified by zinc-finger nucleases targeted to CCR5 control HIV-I in vivo. Nat Biotechnol, 2010. 28(8): p. 839-47.
Hutter, G., et al., Long-term control of HIV by CCR5 Delta321Delta32 stem-cell transplantation. N Engl J Med, 2009. 360(7): p. 692-8.
Kariko, K. et al., Mol Ther 16, 1833-1846 (Nov. 2008).
Khaled, A., et al., Controllable self-assembly of nanoparticles for specific delivery of multiple, therapeutic molecules to cancer cells using RNA nanotechnology. Nano Lett, 2005. 5(9): p. 1797-808.
Kiem, H.P., et al., Foamy combinatorial anti-HIV vectors with MGMTP140K potently inhibit HIV-I and SHIV replication and mediate selection in vivo. Gene Ther, 2010.17(1): p. 37-49.
Kim, R.J., et al., Targeted genome editing in human cells with zinc finger nucleases constructed via modular assembly. Genome Res, IDD9 .19(}}:p. 1279-88.
Kumar, P., et al., T cell-specific siRNA delivery suppresses HIV-I infection in humanized mice. Cell, 2008. 134(4):p. 577-86.
Legrand N., et al., Humanized mice for modeling human infectious disease. challenges, progress, and outlook. Cell Host Microbe, 2009. 6(1): p. 5-9.
Li, MJ., et al., Long-term inhibition of HIV-I infection in primary hematopoietic cells by lentiviral vector delivery of a triple combination of anti-HIV shRNA, anti-CCR5 ribozyme, and a nucleolar localizing TAR decoy. Mol Ther, 2005.12(5): p. 900-9.

(Continued)

*Primary Examiner* — Kimberly Chong
(74) *Attorney, Agent, or Firm* — Perkins Coie LLP; Lara J. Dueppen; Yang Tang

(57) ABSTRACT

An aptamer-mRNA conjugate is provided. The aptamer-mRNA conjugate may include an aptamer component that binds a membrane associated protein on a target cell and an mRNA component that is expressed by the target cell.

12 Claims, 23 Drawing Sheets

Specification includes a Sequence Listing.

(56) References Cited

OTHER PUBLICATIONS

Mayer, G., The chemical biology of aptamers. Angew Chem Int Ed Engl, 2009. 48(15): p. 2672-89.

McNamara II, J. O., et al., Cell type-specific delivery of siRNAs with aptamer-siRNA chimeras. Nat Biotechnol 2006. 24(8): p. 1005-1015.

Moir, S. and A.S. Fauci, B cells in HIV infection and disease. Nat Rev Inununol, 2009.9(4); p. 235-45.

Nazari, R. and S. Joshi, CCR5 as target for HIV-I gene therapy. Curr Gene Ther, 2008.8(4): p. 264-72.

Neff, C. P., et al., An aptamer-siRNA chimera suppresses HIV-1 viral loads and protects from helper CD4+ T cell decline in humanized mice. Sci. Transl. Med. 2011. 3(66): p. 66ra6.

Perez, E.B., et al., Establishment of HIV-I resistance in CD4+ T cells by genome editing using zinc finger nucleases. Nat Biotechnol, 2008. 26(7): p. 808-16.

Richman, D.D., et al., The challenge of finding a cure for HIV infection. Science, 2009.323(5919): p. 1304-7.

Robbins, M.A., et al., Stable expression of shRNAs in human CD34+ progenitor cells can avoid induction of interferon responses to siRNAs in vitro. Nat Biotechnol, 2006.24(5): p. 566-71.

Rossi, JJ., C.R. June, and D.B. Kohn, Genetic therapies against HIV. Nat Biotechnol, 2007. 25(12): p. 1444-54.

Song, R.I., et al., Molecularly cloned SHIV-II 57ipd3N4: a highly replication-competent, mucosally transmissible R5 simian-human immunodeficiency virus encoding HIV clade C Env. J Virol, 2006. 80(17); p. 8729-38.

Thompson, J. S. et al., Science 293, 2108 (Sep. 14, 2001).

Trobridge, G D., et al., Protection of stem-cell-dedved lymphocytes in a primate AIDS gene. Therapy model after in vivo selection. PLoS One, 2009. 4(11): p. e7693.

Tuerk, C. and L. Gold, Systematic evolution of ligands by exponential enrichment: RNA ligands to bacteriophage T4 DNA polymerase. Science, 1990. 249(4968): p. 505-10.

Umov, F.D., et al., Genome editing with engineered zinc finger nucleases. Nat Rev Genet, 2010, 11(9): p. 636-46.

Valeur, B. "Molecular Fluorescence: Principles and Applications," 2001, Wiley-VCH.

Van Duyne, R., et al., The utilization of humanized mouse models for the study of human retroviral infections. Retrovirology, 2009. 6: p. 76.

Warren, L., et al., Highly efficient reprogramming to pluripotency and directed differentiation of human cells with synthetic modified mRNA. Cell Stem Cell Nov. 5, 2010;7(5):618-30.

Wu, J., et al., Polycationic dendrimers interact with RNA molecules: polyamine-dendrimers inhibit the catalytic activity of Candida ribozymes. Chem Commun (Camb), 2005(3): p. 313-5.

Xue, Y.N., et al., Improving gene delivery efficiency of bioreducible poly(amidoamine)s via grafting with dendritic poly(amidoamine)s. Macromol Biosci, 2010.10(4): p. 404-14.

Zhou, J., et al., Novel dual inhibitory function aptamer-siRNA delivery system for HIV-I therapy. Mol Ther, 2008.16(8): p. 1481-9.

Zhou, J, et al., Selection, characterization and application of new RNA HIV gp 120 aptamers for facile delivery of Dicer substrate siRNAs into HIV infected cells. Nucleic Acids Res, 2009. 37(9): p. 3094-109.

Zhou, J. and JJ. Rossi, Bivalent aptamers deliver the punch. Chem Biol, 2008.15(7): p. 644-5.

Zhou, J., et al., PAMAM dendrimers for efficient siRNA delivery and potent gene silencing. Chem Commun (Camb), 2006(22): p. 2362-4.

SEQUENCE LISTING

```
<160> NUMBER OF SEQ ID NOS: 2

<210> SEQ ID NO 1
<211> LENGTH: 81
<212> TYPE: RNA
<213> ORGANISM: Artificial Sequence
<220> FEATURE:
<223> OTHER INFORMATION: Synthetic aptamer sequence A-1

<400> SEQUENCE: 1
gggaggacga ugcggaauug agggaccacg cgcugcuugu ugugauaagc aguuugucgu      60
gauggcagac gacucgcccg a                                                81

<210> SEQ ID NO 2
<211> LENGTH: 81
<212> TYPE: RNA
<213> ORGANISM: Artificial Sequence
<220> FEATURE:
<223> OTHER INFORMATION: Synthetic aptamer sequence B-68

<400> SEQUENCE: 2
gggaggacga ugcggacaua guaaugacac ggaggaugga gaaaaaacag ccaucucuug      60
acggucagac gacucgcccg a                                                81
```

APTAMER-MRNA CONJUGATES FOR TARGETED PROTEIN OR PEPTIDE EXPRESSION AND METHODS FOR THEIR USE

PRIORITY CLAIM

This application is a divisional of U.S. application Ser. No. 14/541,639, filed Nov. 14, 2014, which is a divisional of U.S. application Ser. No. 13/494,880, filed Jun. 12, 2012, now issued as U.S. Pat. No. 8,916,696, issued Dec. 23, 2014, which claims priority to U.S. Provisional Application No. 61/496,027 filed Jun. 12, 2011, the subject matter of which is hereby incorporated by reference as if fully set forth herein.

STATEMENT OF GOVERNMENT INTEREST

The present invention was made with government support under Grant Nos. AI29329, AI42552 and HL07470 awarded by the National Institutes of Health. The Government has certain rights in the invention.

BACKGROUND

Gene therapy, or genetic engineering, is the insertion, alteration, or removal of genes within an individual's cells and biological tissues to treat disease. It is a technique for correcting defective genes that are responsible for disease development. The most common form of genetic engineering involves the insertion of a functional gene at an unspecified location in the host genome. This is accomplished by isolating and copying the gene of interest, generating a construct containing all the genetic elements for correct expression, and then inserting this construct into a random location in the host organism.

Other forms of genetic engineering include gene targeting and knocking out specific genes via engineered nucleases such as zinc finger nucleases, engineered I-CreI homing endonucleases, or nucleases generated from TAL effectors. An example of gene-knockout mediated gene therapy is the knockout of the human CCR5 gene in T-cells in order to control HIV infection. The use of gene therapy for the treatment of HIV-1 infection received a huge boost when it was demonstrated that HIV-1 infection could be eradicated from an AIDS/leukemia patient who received an allogeneic hematopoietic stem cell transplant from a donor who had a homozygous deletion in the chemokine receptor gene CCR5 [2]. It is known that CCR5 is a primary co-receptor for HIV-1 entry, so the transplant patient was, in effect, given a protective therapy. Although this is a single patient result, the idea that repopulation of the hematopoietic system with cells resistant to HIV-1 infection can have a major impact on the disease is being investigated. Finding CCR5–\– compatible donors is a major challenge and as such this cannot be considered to be a treatment that will have broad applications. In addition, virus that mutates to CXCR4 tropism can infect the CCR5–\– cells and reactivate the infection.

Treatment of disease using genetic engineering has been met with limited success, as there are several challenges that prevent gene therapy from being more successful. Some of these challenges include (1) problems with integrating therapeutic DNA into the genome and the rapidly dividing nature of many cells prevent gene therapy from achieving any long-term benefits; (2) problems with the use of viral vectors, which are the carrier of choice in most gene therapy studies, including toxicity, virulence, immune and inflammatory responses, and issues with gene control and targeting; and (3) the chance of inducing a tumor by insertional mutagenesis. If the DNA is integrated in the wrong place in the genome, for example in a tumor suppressor gene, it could induce a tumor.

In addition to gene therapy, therapeutic strategies designed to combat HIV/AIDS have primarily relied upon small molecule drugs. Although some highly active antiretroviral therapy (HAART) treatments for HIV-1 have been therapeutically effective in the majority of patients, drug resistance and toxicity remain a concern with some individuals not responding to such therapy [1]. Alternative therapeutic strategies need to be developed to overcome these limitations.

Thus, it is of importance to find alternative approaches for delivery of therapeutic proteins or peptides in a combinatorial gene therapy setting.

SUMMARY

In one embodiment, an aptamer-mRNA conjugate is provided. The aptamer-mRNA conjugate may include an aptamer component that binds a membrane associated protein on a target cell and an mRNA component that is expressed by the target cell.

In another embodiment, a method for treating a disease is provided. The method may include administering a therapeutically effective dose of a pharmaceutical composition to a subject suffering from a disease, wherein the pharmaceutical composition comprises one or more aptamer-mRNA conjugates described herein. In some aspects the disease is cancer, a chronic viral infection or a genetic disorder.

In another embodiment, a method for imaging a disease, such as cancer, viral infection or a genetic disorder is provided. The method may include administering an effective dose of one or more aptamer-mRNA conjugates to a subject and exposing the subject to an imaging method. The imaging method may be positron emission tomography (PET), computer assisted tomography (CAT), single photon emission computerized tomography, x-ray, fluoroscopy, or magnetic resonance imaging (MRI).

DETAILED DESCRIPTION

Figure 1A:
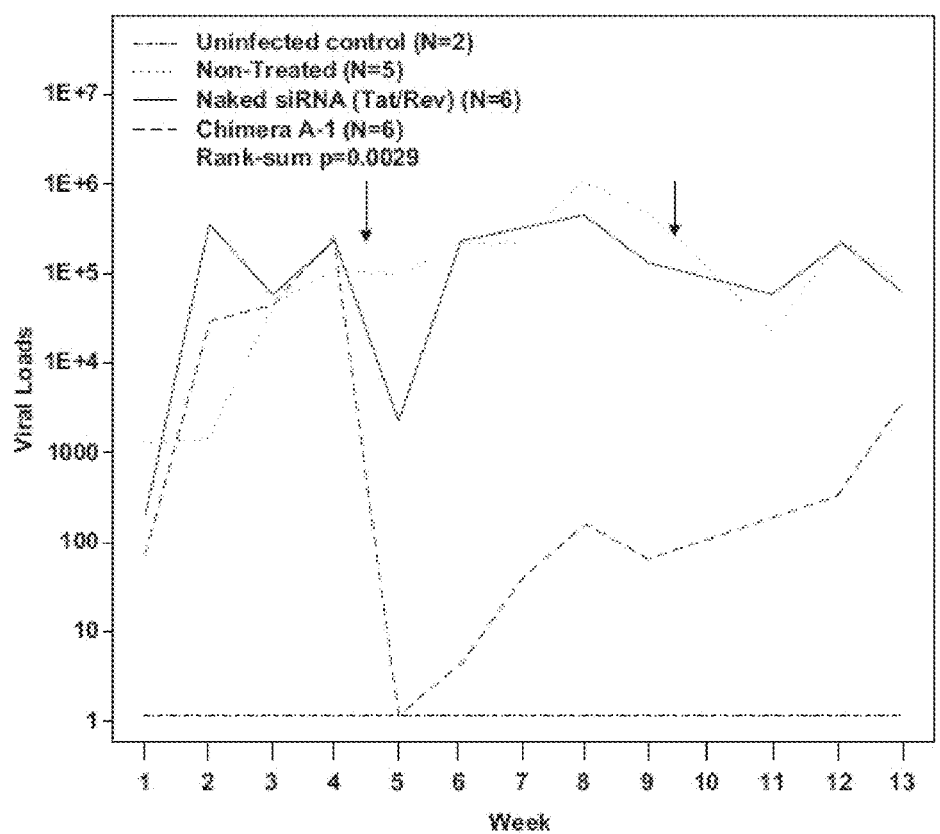
FIGS. 1 A-B illustrate that anti-gp120 aptamer and aptamer-tat/rev chimera Ch A-1, but not mutant aptamer-tat/rev, suppress viral loads in HIV-1 infected RAG-hu mice. HIV-1 viral loads at different weeks post infection and treatment are indicated. The treatment period is indicated by the yellow framed-in region. (A) The viral loads of uninfected mice (n=2), non-treated mice (n=5), naked tat/rev siRNA treated mice (n=6) and anti-gp120 aptamer-tat/rev chimera (Ch A-1) treated mice (n=6) are indicated (8). Relative antiviral activities of A1 Aptamer, Ch A1 chimera and mutant A-5 aptamer chimera (A) viral loads at each indicated week pre- and post-treatment. Weeks post-injection and the time point of treatment start and end are indicated. The viral loads of uninfected mice (n=2), non-treated mice (n=3), aptamer A-1 treated mice (n=3), mutant gp120 aptamer-tat/rev chimera (Ch A-5) treated mice (n=3) and anti-gp120 aptamer-tat/rev chimera (Ch A-1) treated mice (n=3) are indicated. P values for both experiments are indicated. Vertical arrows indicate beginning and ending of treatment period.

According to some embodiments, an aptamer-mRNA conjugate is provided herein that includes an aptamer component conjugated to an mRNA component. As used herein, the term "conjugated to," or "conjugate" refers to two or more entities or the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g. charge interactions, affinity interactions, metal coordination, physical adsorption, host-guest interactions, hydrophobic interactions, PI stacking interactions, hydrogen bonding interactions such as with "sticky sequences," van der Waals interactions, magnetic interactions, electrostatic interactions, dipole-dipole interactions, etc.).

The aptamer-mRNA conjugate binds a membrane associated protein. In some embodiments, a membrane associated protein is an antigen on the surface of a cell, such as a cell surface receptor, an integrin, a transmembrane protein, an ion channel, a membrane transport protein, or a glycoprotein. In some aspects, the membrane associated protein is endocytosed and internalized by a target cell upon binding of the aptamer-mRNA conjugate. Once internalized, the mRNA component of the conjugate enters the translational pathway of the target cell and is expressed as a peptide or protein. Such a peptide or protein may be used for treatment of a condition or disease, determining the function of the peptide or protein, for imaging cells for diagnosing or monitoring a condition or disease in vivo. Specific delivery of these aptamer-mRNA conjugates provide a transient, less toxic and less mutagenic alternative to gene therapy because viral vectors are not needed and the genome of the target cells is left intact.

Aptamer Component

In one embodiment, the aptamer-mRNA conjugate includes an aptamer component for targeting particular cells. An "aptamer" is any suitable small molecule, such as a nucleic acid or a peptide molecule that binds specifically to a target, such as a small molecule, protein, nucleic acid, cell, tissue or organism. Aptamers that target specific cell surface proteins can be employed as delivery molecules to target a distinct cell type, thereby reducing off-target effects or other unwanted side effects. Further, by binding a specific cell surface protein, aptamers may also be used as a therapeutic agent on their own.

In some embodiments, the aptamer component is a nucleic acid aptamer. Such aptamers with binding affinities in nanomolar range have been utilized for flexible applications ranging from diagnostic to therapeutic assay formats (Zhou & Rossi 2009). Moreover, aptamers that target specific cell surface proteins are employed as delivery molecules to target a distinct cell type, hence reducing off-target effects or other unwanted side effects (Zhou et al. 2008; McNamara et al. 2006).

The nucleic acid that forms the nucleic acid aptamer may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid aptamer can be replaced with a hydrocarbon linker or a polyether linker provided that the binding affinity and selectivity of the nucleic acid aptamer is not substantially reduced by the substitution.

Nucleic acids in accordance with the embodiments described herein may include nucleotides entirely of the types found in naturally occurring nucleic acids, or may instead include one or more nucleotide analogs or have a structure that otherwise differs from that of a naturally occurring nucleic acid. U.S. Pat. Nos. 6,403,779, 6,399,754, 6,225,460, 6,127,533, 6,031,086, 6,005,087, 5,977,089, disclose a wide variety of specific nucleotide analogs and modifications that may be used, and are hereby incorporated by reference as if fully set forth herein. Also see Crooke, S. (ed.) Antisense Drug Technology: Principles, Strategies, and Applications (1st ed.), Marcel Dekker; ISBN: 0824705661; 1st edition (2001), which is also hereby incorporated by reference as if fully set forth herein. For example, 2'-modifications include halo, alkoxy and allyloxy groups. In some embodiments, the 2'—OH group is replaced by a group selected from H, OR, R, halo, SH, SR, $NH_2$, NHR, $NR_2$ or CN, wherein R is $C_1$-$C_6$ alkyl, alkenyl, or alkynyl, and halo is F, Cl, Br, or I. Examples of modified linkages include phosphorothioate and 5'-N-phosphoramidite linkages.

Nucleic acids having a variety of different nucleotide analogs, modified backbones, or non-naturally occurring internucleoside linkages can be utilized in accordance with the embodiments described herein. Nucleic acids may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothym idine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. The nucleotide analogs or other modification(s) may be located at any position(s) of a nucleic acid such that the function of the nucleic acid is not substantially affected. To give but one example, modifications may be located at any position of an aptamer component such that the ability of the aptamer to specifically bind to the target is not substantially affected. The modified region may be at the 5'-end and/or the 3'-end of one or both strands. For example, modified nucleic acid aptamers in which approximately 1-5 residues at the 5' and/or 3' end of either of both strands are nucleotide analogs and/or have a backbone modification have been employed. The modification may be a 5' or 3' terminal modification.

Selection of aptamers may be accomplished by any suitable method known in the art, including an optimized protocol for in vitro selection, known as SELEX (Systemic Evolution of Ligands by Exponential enrichment). Although the SELEX process has been established as a general technique for aptamer selection, it is not predictable nor is it standardized for use with any target. Instead, the SELEX process must be optimized and customized for each particular target molecule. Each SELEX experiment includes its own challenges and is not guaranteed to work for all targets.

Many factors are important for successful aptamer selection. For example, the target molecule should be stable and easily reproduced for each round of SELEX, because the SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the SELEX process for a single target may need to be repeated with different starting libraries. Aptamer selection using SELEX is unpredictable. Even when all of the factors are optimized for successful aptamer selection, the SELEX process does not always yield viable aptamers for every target molecule.

According to the embodiments described herein, the aptamer component of the aptamer-mRNA conjugates described herein is an aptamer that targets specifically binds an endocytotic membrane associated protein, (e.g., a membrane receptor or a glycoprotein) that is solely expressed on or is overexpressed on a particular cell type for selective delivery of the aptamer-mRNA conjugates. Membrane associated proteins that may be targeted by the aptamer component include, but are not limited to, CD4 (T cell), CD19 (B cell), dendritic cell-specific intercellular adhesion molecule-3-grabbing non-integrin (DC-SIGN/CD209) (dendritic cells), HIV envelope glycoprotein gp120 (HIV-infected cells), CCR5, endothelial growth factor receptor (EGFR/ErbB1), endothelial growth factor receptor 2 (EGFR2/ErbB2/HER2), endothelial growth factor receptor 3 (EGFR3/ErbB3), endothelial growth factor receptor 4 (EGFR4/ErbB4), endothelial growth factor receptor variant III (EGFRvIII), Transferrin Receptor, prostate specific membrane antigen (PSMA), vascular endothelial growth factor (VEGF), vascular endothelial growth factor 2 (VEGF-2), IL-2 receptor (CD25), CD11a, CD33, CD20, CD3 receptor, CD52, carcinoembryonic antigen (CEA), tumor associated glycoprotein 72 (TAG-72), low density lipoprotein (LDL) receptor, insulin receptor, megalin receptor, lipoprotein receptor related protein (LRP), mannose receptor, P63/CKAP4 receptor, arrestin, asialoglycoprotein (ASGP), gastrin/cholecystokinin B receptor (CCK-B), hepatocyte growth factor receptor (HGFR), recepteur d'origine nantais (RON) receptor, Fibroblast Growth Factor Receptor (FGFR), Insulin Like Receptor (ILR), α-Fetoprotein (AFP), CA125/MUC16, platelet derived growth factor receptor (PDGFR), stem cell factor receptor, colony stimulating factor-1 receptor, integrins, toll-like receptors (TLR), B cell antigen receptor (BCR), tumor necrosis factor α (TNFα) receptor, and any other suitable entocytotic membrane associated protein.

Figure 17:
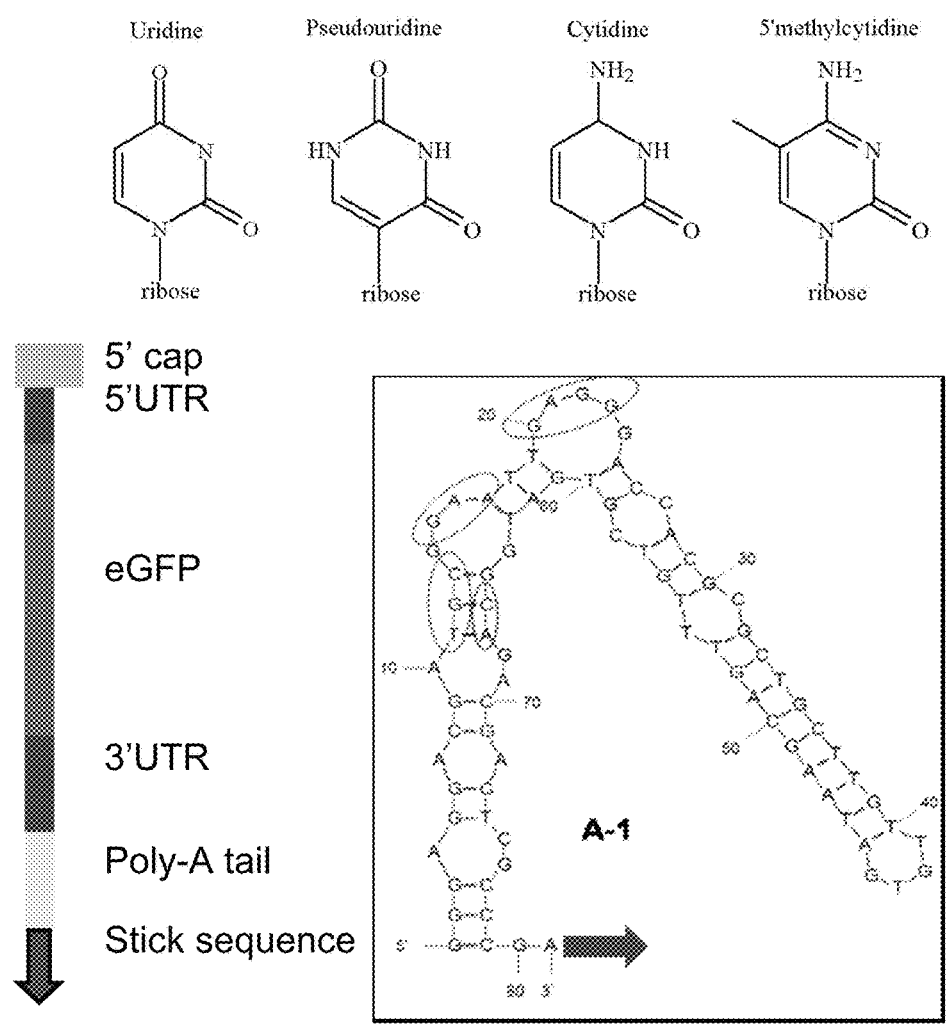
FIG. 17 illustrates the design of synthetic mRNA.

In one embodiment, the aptamer component of the aptamer-mRNA conjugate described herein is a B cell specific aptamer that targets and binds BAFF-R. One example of a BAFF-R aptamer according to the embodiments described herein is shown in FIG. 17. Additional examples of BAFF-R aptamers may be found in PCT Application No. PCT/US11/32385, filed Apr. 13, 2011, which is hereby incorporated by reference in its entirety as if fully set forth herein. In another embodiment, the aptamer component of the aptamer-mRNA conjugate described herein is an anti-HIV aptamer (e.g., gp120 or CCR5) that targets and binds an infected cell, a free HIV virus or both. Examples of anti-HIV aptamers can be found in Zhou et al., Nucleic Acids Res, 2009. 37(9): p. 3094-109, which is hereby incorporated by reference in its entirety as if fully set forth herein.

mRNA Component

In some embodiments, the aptamer-mRNA conjugate includes an mRNA component that includes an mRNA molecule that is expressed intracellularly as part of a therapeutic or diagnostic payload. Alternatively, the mRNA component may include a cDNA molecule. Further, the mRNA component may express a full wild type protein or peptide in a target cell, or may express at least the biologically active portion of the protein or peptide.

In some embodiments, the mRNA component acts as a therapeutic agent to express a protein or peptide that is missing or altered due to a genetic disorder that arises from a mutation or deletion in a corresponding gene. In this case, the protein or peptide that is expressed by the mRNA component serves to replace the missing protein or to provide a normal protein to compete with the altered or mutated version in a cell that is lacking a normal version of the protein or peptide. In some embodiments, the mRNA expresses a protein or peptide associated with a single gene disorder, including, but not limited to, clotting factors (e.g., Factor IX or Factor VIII), cystic fibrosis transmembrane conductance regulator, α-1-antitrypsin, β-globulin, fibrillin-1, spectrin, ankyrin, band 3 protein, huntingtin, galactose-1-phosphate uridyl transferase, galactokinase, UDP galactose epimerase, glygogen synthase, glucose-6-phosphatase, acid maltase, glycogen debrancher, glycogen branching enzyme, muscle glycogen phosphorylase, liver glycogen phosphorylase, muscle phosphofructokinase, phosphorylase kinase (PHKA2), glucose transporter (GLUT2), aldolase A, β-enolase, glycogen synthase, glycosaminoglycans, insulin, phenylalanine hydroxylase, hexoaminidase A, haemoglobin, apolipoprotein A, neurofibromin and dystrophin.

In other embodiments, the mRNA component acts as a therapeutic agent to express an altered or mutated protein or peptide using a "protein mutagenesis" approach. In this case, a deliberate change is made in the protein structure that is directed toward one or more specific amino acid residues. The altered or mutated protein may be used to study protein function in vitro or in vivo, but may also be used as a therapeutic agent to express a protein or peptide that has improved properties for therapeutic uses (e.g., improved affinity to a target or improved catalytic or kinetic properties).

In some embodiments, the mRNA component acts as a therapeutic agent to express a cytotoxic protein or peptide to kill a cancer cell or a virally infected cell. In contrast to other systemic cytotoxic therapeutic regimens such as cancer chemotherapy, which kills both cancerous and healthy cells, the aptamer component of the aptamer-mRNA conjugate can target and selectively deliver a therapeutic to kill cancerous cells.

In some embodiments, the mRNA component may express a bacterial cytotoxin including, but not limited to, an alpha-pore forming toxin (e.g., cytolysin A from *E. coli*), a beta-pore-forming toxin (e.g., α-Hemolysin, PVL—panton Valentine leukocidin, aerolysin, clostridial Epsilon-toxin, *clostridium perfringens* enterotoxin), binary toxins (anthrax toxin, edema toxin, *C. botulinum* C2 toxin, *C spirofome* toxin, *C. perfringens* iota toxin, *C. difficile* cyto-lethal toxins (A and B)), prion, parasporin, a cholesterol-dependent cytolysins (e.g., pneumolysin), a small pore-forming toxin (e.g., Gramicidin A), a cyanotoxin (e.g., microcystins, nodularins), a hemotoxin, a neurotoxin (e.g., botulinum neurotoxin), a cytotoxin, cholera toxin, diphtheria toxin, *Pseudomonas* exotoxin A, tetanus toxin, and an immunotoxin (idarubicin, ricin A, CRM9, Pokeweed antiviral protein, DT).

In some embodiments, the mRNA component may express a cytotoxic peptide or peptide related to the immune system including, but not limited to, a cytotoxic T cell or B cell epitope to stimulate a specific immune response via presentation of such epitope with an MHC I complex, an membrane attack complex protein (MAC) of the complement system, perforin, a granzyme and a granulysin.

In some embodiments, the mRNA component may express an apoptotic triggering protein or peptide including, but not limited to, apoptotic protease activating factor-1 (Apaf-1), cytochrome-c, caspase initiator proteins (CASP2, CASP8, CASP9, CASP10), apoptosis inducing factor (AIF), p53, p73, p63, Bcl-2, Bax, granzyme B, poly-ADP ribose polymerase (PARP), and P 21-activated kinase 2 (PAK2).

In other embodiments, the mRNA component acts as a therapeutic agent to express a protein or peptide that targets and inhibits, cleaves or neutralizes a pathological moiety such as a virus-associated protein (e.g., CCR5, gp120), a free virus (e.g., HIV, CMV), a protein associated with a particular disease or a protein expressed by an oncogene or proto-oncogene (e.g., ABL, Src-family of tyrosine kinases, Syk-ZAP-70 family of tyrosine kinases, BTK family of tyrosine kinases, Raf kinase, cyclin-dependent kinases, Ras, myc, and STAT3). A protein, peptide, antibody or functional fragment thereof that targets and inhibits, cleaves or neutralizes such a pathological moiety may include restriction enzymes or endonucleases such as Zn finger endonucleases and homing endonucleases.

An "antibody or functional fragment thereof" as used herein refers to an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, tetrabodies, tandem di-scFv, tandem tri-scFv). The term functional antibody fragment includes antigen binding fragments of antibodies including, but not limited to, fragment antigen binding (Fab) fragment, F(ab')$_2$ fragments, Fab' fragments, Fv fragments, recombinant IgG (rIgG) fragments, single chain variable fragment (scFv) and single domain antibodies (e.g., sdAb, sdFv, nanobody) fragments.

In some embodiments, the mRNA component acts as a diagnostic agent to express a protein or peptide that may be used to target and visualize cells in vivo via an imaging method (e.g., positron emission tomography (PET), computer assisted tomography (CAT), single photon emission computerized tomography, x-ray, fluoroscopy, and magnetic resonance imaging (MRI)) for diagnosing or visualizing a disease.

In some embodiments, a diagnostic agent may be a fluorescent, luminescent, or magnetic protein, peptide or derivatives thereof (e.g., genetically engineered variants). Fluorescent proteins that may be expressed by the mRNA component include green fluorescent protein (GFP), enhanced GFP (eGFP), red, blue, yellow, cyan, and sapphire fluorescent proteins, and reef coral fluorescent protein. Luminescent proteins that may be expressed by the mRNA component include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9.sup.th edition, 2002; and The Handbook—A Guide to Fluorescent Probes and Labeling Technologies, Invitrogen, 10th edition, available at the Invitrogen web site; both of which are hereby incorporated by reference as if fully set forth herein.)

In some aspects, the mRNA component may be further conjugated to or otherwise associated with a non-protein diagnostic agent or a delivery vehicle such as a nanoparticle. According to the embodiments described herein, the additional diagnostic agents may include, but are not limited to, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, it should be noted that some nanoparticles, for example quantum dots and metal nanoparticles (described below) may also be suitable for use as a detection agent.

Fluorescent and luminescent substances that may be used as an additional diagnostic agent in accordance with the embodiments of the disclosure include, but are not limited to, a variety of different organic or inorganic small molecules commonly referred to as "dyes," "labels," or "indicators." Examples include fluorescein, rhodamine, acridine dyes, Alexa dyes, and cyanine dyes.

Enzymes that may be used as an additional diagnostic agent in accordance with the embodiments of the disclosure include, but are not limited to, horseradish peroxidase, alkaline phosphatase, acid phoshatase, glucose oxidase, β-galactosidase, β-glucoronidase or β-lactamase. Such enzymes may be used in combination with a chromogen, a fluorogenic compound or a luminogenic compound to generate a detectable signal.

Radioactive substances that may be used as an additional diagnostic agent in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Se, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as an additional diagnostic agent in accordance with the embodiments of the disclosure include, but are not limited to, ions of transition and lanthanide metals (e.g. metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the diagnostic agent is a radioactive metal or paramagnetic ion, the agent may be reacted with a reagent having a long tail with one or more chelating groups attached to the long tail for binding these ions. The long tail may be a polymer such as a polylysine, polysaccharide, or other derivatized or derivatizable chain having pendant groups to which may be bound to a chelating group for binding the ions. Examples of chelating groups that may be used according to the disclosure include, but are not limited to, ethylenediam inetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups. The chelate is normally linked to the PSMA antibody or functional antibody fragment by a group which enables formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis.

Contrast agents that may be used as an additional diagnostic agent in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

In some embodiments, expression of the mRNA component may be controlled by conjugating the mRNA to a "riboswitch" that is triggered by an effector compound. Examples of riboswitches that may be used in accordance with the embodiments described herein may be found in U.S. Pat. No. 7,794,931. Other methods for controlling the expression of the mRNA component within the target cell are known in the art, such as conjugating the mRNA to a nucleic acid sequence of an iron binding protein.

Aptamer-mRNA Conjugate Carriers

In other embodiments, the mRNA may be associated with a dendrimer (e.g., Poly(amidoamine) ("PAMAM")) or a nanoparticle. The physical characteristics of dendrimers, including their monodispersity, water solubility, encapsulation ability, and large number of functionalizable peripheral groups, make these macromolecules appropriate candidates for evaluation as drug delivery vehicles. There are at least three methods for using dendrimers in drug delivery: first, the drug (e.g. the aptamer-mRNA conjugate) is covalently attached to the periphery of the dendrimer to form dendrimer prodrugs, second the drug is coordinated to the outer functional groups via ionic interactions, or third the dendrimer acts as a unimolecular micelle by encapsulating a pharmaceutical through the formation of a dendrimer-drug supramolecular assembly. The use of dendrimers as drug carriers by encapsulating hydrophobic drugs is a potential method for delivering highly active pharmaceutical compounds that may not be in clinical use due to their limited water solubility and resulting suboptimal pharmacokinetics.

The term "nanoparticle" refers to a microscopic particle whose size is measured in nanometers, e.g., a particle with at least one dimension less than about 100 nm. Nanoparticles are particularly useful as detectable substances because they are small enough to scatter visible light rather than absorb it. For example, gold nanoparticles possess significant visible light extinction properties and appear deep red to black in solution. As a result, aptamer-mRNA conjugates that are further conjugated to nanoparticles can be used for the in vivo imaging of tumors or cancerous cells in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to a PSMA antibody or functional antibody fragment, can be used as imaging agents for the in vivo detection of tumor cells as described above. Alternatively, nanoparticles can be used in therapeutic applications as drug carriers that, when conjugated to an aptamer component of the present disclosure, deliver the mRNA component and optionally other chemotherapeutic agents, hormonal therapeutic agents, radiotherapeutic agents, toxins, or any other cytotoxic or anti-cancer agent known in the art.

Methods for Treating or Imaging a Disease

In some embodiments, methods for treating a disease are provided. Such methods may include administering a therapeutically effective dose of a pharmaceutical composition to a subject suffering from a disease, wherein the pharmaceutical composition includes one or more aptamer-mRNA conjugates as described in detail above. The disease may be cancer, chronic viral infection, chronic infectious disease affecting a particular cell type, or any genetic disease that is associated with a mutated, altered, missing, or overexpressed, gene or protein.

Cancers and tumor types that may be treated in accordance with the embodiments described herein include but are not limited to bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma (B cell and T cell) and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to treat tumors that are malignant (e.g., cancers) or benign (e.g., hyperplasia, cyst, pseudocyst, hamartoma, and benign neoplasm).

Genetic disorders that may be treated in accordance with the embodiments described herein include, but are not limited to, muscular dystrophy, hemophilia, Huntington's disease, alpha-1 antitrypsin deficiency, Alzheimer's disease, various forms of breast cancer (e.g., BRCA1), cystic fibrosis, galactosemia, congenital hyperthyroidism, maple syrup urine disease, neurofibromatosis I, phenylketonuria, sickle cell disease, and Smith-Lemli-Opitz (SLO-RSH) syndrome, familial hypercholesterolemia, polycystic kidney disease, hereditary spherocytosis, Marfan syndrome, Tay-Sachs disease, mucopolysacchariddoses, and glycogen storage diseases.

Viruses and virally infected cells that may be treated in accordance with the embodiments described herein include, but are not limited to, hepatitis, papillomavirus, herpes simplex virus (HSV), cytomegalovirus (CMV), Epstein-Barr virus (EBV), Smallpox virus, and human or simian immunodeficiency virus (HIV/SHIV).

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "therapeutically effective amount" or a "therapeutically effective dose is an amount of a compound that produces a desired therapeutic effect in a subject, such as preventing or treating a target condition or alleviating symptoms associated with the condition. The most effective results in terms of efficacy of treatment in a given subject will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $21^{st}$ Edition, Univ. of Sciences in Philadelphia (USIP), Lippincott Williams & Wilkins, Philadelphia, Pa., 2005.

According to the embodiments described herein, the pharmaceutical composition may optionally include, in addition to the one or more aptamer-mRNA conjugates, one or more therapeutic agents, such as an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and antiadhesion molecules), inhibitors of DNA, RNA, or protein synthesis.

In some embodiments, the pharmaceutical composition may also include a pharmaceutically acceptable carrier. A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

In some embodiments, methods for imaging a disease are provided. Such methods may include administering an effective dose of one or more aptamer-mRNA conjugates as described in detail above to a subject and exposing the subject to an imaging method. Imaging methods may include, but are not limited to, positron emission tomography (PET), computer assisted tomography (CAT), single photon emission computerized tomography, x-ray, fluoroscopy, and magnetic resonance imaging (MRI), each of which may be used with the method for diagnosing or visualizing a disease.

The methods described herein may be used in combination with one or more additional treatment methods. In one embodiment, the aptamer-mRNA conjugate treatment may be combined with a treatment involving siRNA delivery. This way, one could effectively silence a mutated gene with an aptamer-siRNA conjugate and replace the mutated gene with a normal expressed protein or peptide using an aptamer-mRNA described herein.

Use of Aptamers for Targeting Viruses

As discussed above, the aptamer component of an aptamer-mRNA conjugate according to some embodiments may target a free virus to prevent infection, a virally infected cell or both. For example, an anti-gp120 aptamer or a chemokine receptor gene CCR5 aptamer may be used as a dual function inhibitor of simian/human immunodeficiency virus (SHIV) via neutralization of free virus and, when conjugated to an mRNA, via selective delivery of a SHIV targeting mRNA such as homing endonuclease mRNAs and Zn-finger nucleases to uninfected CD4+ cells via a CD4 specific aptamer.

Recent developments in targeted disruption of genetic information via the use of sequence specific Zn finger nucleases and homing endonucleases [5-10] illustrate that it is possible to disrupt coding or regulatory regions rendering genes nonfunctional. Introducing site specific nucleases that selectively target SHIV sequences into a target cell, should result in inactivation of viral transcription and lead to lowering of viral loads. One major issue with this technology is the challenge of delivering these endonucleases to the target cells in vivo. Thus, the development of strategies to deliver anti HIV/SHIV nucleases is an important aspect for effective treatment with such agents. When administered to a human, the aptamer-mRNA conjugates using the approach described herein may be able to purge HIV-1 reservoirs from infected individuals.

Aptamers, such as nucleic acid aptamers, represent a new and potentially potent class of anti-HIV drugs. Ribonucleic acid (RNA) aptamers are selected from random sequence pools of RNAs under conditions that provide highly specific, tight binding to targeted molecules. [11-12]. The low nanomolar binding affinities and exquisite binding specificity of aptamers to their targets have made them versatile tools for diagnostics, in vivo imaging, and therapeutics [13-14]. It was previously demonstrated that an anti-HIV-1 gp120 aptamer can neutralize HIV-1 infection and is also capable of delivering anti-HIV siRNAs into HIV-1 infected cells [15-16]. The ability of these anti-gp120 aptamers may be tested for additional or dual functions: neutralization of free virus (SHIV in this study) and selective delivery of backbone modified Zn finger and homing endonucleases encoding mRNAs to HIV-1 infected cells. As described in the Examples below, the use of a CD4 specific aptamer for cell type specific delivery of an anti-CCR5 Zn finger nuclease mRNA to PBMCs is provided. This approach may be used in vivo to generate a therapeutic or prophylactic agent that, when administered, provides a population of HIV-1 resistant cells.

In some embodiments, G5 PAMAM flexible dendrimers may also be used to deliver anti-CCR5 and anti-HIV Zn finger and homing endonuclease cDNAs or mRNAs to CD4+ lymphocytes. The dendrimers may also be conjugated to an aptamer, such as an anti-gp120 aptamer or an anti-CCR5 aptamer for a selective delivery of the mRNAs. The dendrimers for delivery of transiently expressed cDNAs or mRNAs to cells encoding Zn finger and homing endonucleases into T-lymphocytes to inactivate integrated proviral DNA in SHIV infected cells or the CCR5 gene in uninfected cells.

Recently, the use of G5 PAMAM flexible dendrimers for the delivery of siRNAs into CD4+ lymphocytes has been tested. The siRNAs have been functionally delivered to the cytoplasm of primary T-cells both in cell culture and in vivo. These same PAMAM dendrimers may also been used to deliver cDNAs into human cells. In addition, the dendrimers may be used as an alternative and possibly complementary approach for delivery of the endonuclease cDNAs and mRNAs both in vitro and in vivo. This delivery may be accomplished in a subject that has an HIV infection, may develop an HIV infection, or is at risk of developing an HIV infection, such as humans and humanized mice. The studies described in the Examples below illustrate a complementary approach for using exogenously delivered Zn finger nucleases and homing endonucleases for sequence specific inactivation of the targeted genetic elements as treatments for preventing and eradicating viral infection.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. For example, although the Examples describe studies related to aptamer-mRNA conjugates using aptamers to gp120, CD4 and to BAFF-R, once skilled in the art would understand that any aptamer may be conjugated to any applicable mRNA molecule based on the methods described below in order to express a protein in a target cell. Non-limiting examples of aptamers and mRNA molecules that may be used are described above. Further, all references cited in the disclosure are hereby incorporated by reference in their entirety, as if fully set forth herein.

EXAMPLES

Example 1: An Anti-gp120 Aptamer-siRNA Chimera Demonstrates Potent Inhibition of HIV-1 Replication, Functional Delivery of the siRNA, and Protection Against HIV-1 Mediated T-Cell Depletion To illustrate that aptamers against gp120 are able to target free virus and/or HIV infected cells in vivo, studies using anti-HIV-1 gp120 aptamers as HIV-1 inhibitory agents and as vectors for delivery of siRNAs into HIV-1 infected lymphocytes were performed [16]. An important step in the development of the anti-gp120 aptamer as a therapeutic agent for inhibition of HIV-1 infection is to validate the anti-HIV efficacy in an in vivo model. The newly developed humanized Rag2-ryc-r (RAG-hu) mouse model with a capacity for multi-lineage human hematopoietic cell engraftment is one in vivo model that may be used [17-22]. Previous studies have demonstrated that HIV-1 infected RAG-hu mice can sustain long-term viremia lasting for more than a year and display a continuous declining trend of CD4 T-cell levels as seen in humans [23]. Moreover, in contrast to established SCID-hu and hu-PBLSCID mouse models, which are models for acute infection, HIV-1 infection of RAG-hu mice leads to chronic viremia and persistent CD4 T-cell loss [17]. Prolonged viremia combined with CD4 T-cell depletion in this system mirrors the main features of human HIV-1 infection. Therefore, this system was used to test the in vivo efficacy of a gp120 aptamer by first creating viremic animals with HIV-1 NL 4-3 infection, followed by intravenous injections of 6 μgms of the aptamer and aptamer siRNA chimera with 2' Fluoro backbone modifications, per animal.

First, the anti-HIV-1 activity of a chimeric RNA, Ch A-1 (described in Zhou et al., Nucleic Acids Res, 2009. 37(9): p. 3094-109, which is hereby incorporated by reference in its entirety as if fully set forth herein) was compared to the activity of an anti-tat/rev siRNA as an RNA injection control. Six animals were given five weekly injections of 0.25 nmols Ch A-1 or tat/rev siRNA alone. Plasma viral loads were monitored at various times to determine the treatment efficacies (FIG. 1A). A general pattern of decreased viral loads was seen in the majority of chimera Ch A-1 treated mice compared to the HIV-1 infected, untreated and siRNA treated controls, and this reached statistical significance with a rank sum P=0.0029. The viral loads were suppressed to below detectable levels in all the chimera treated mice within a week post treatment (week 5 as shown) and this marked viral suppression persisted throughout the treatment period in the majority of mice. Four out of six mice had undetectable viral loads even up to three weeks post-treatment, indicating the sustained efficacy of the Ch A-1 chimera.

Figure 1B:
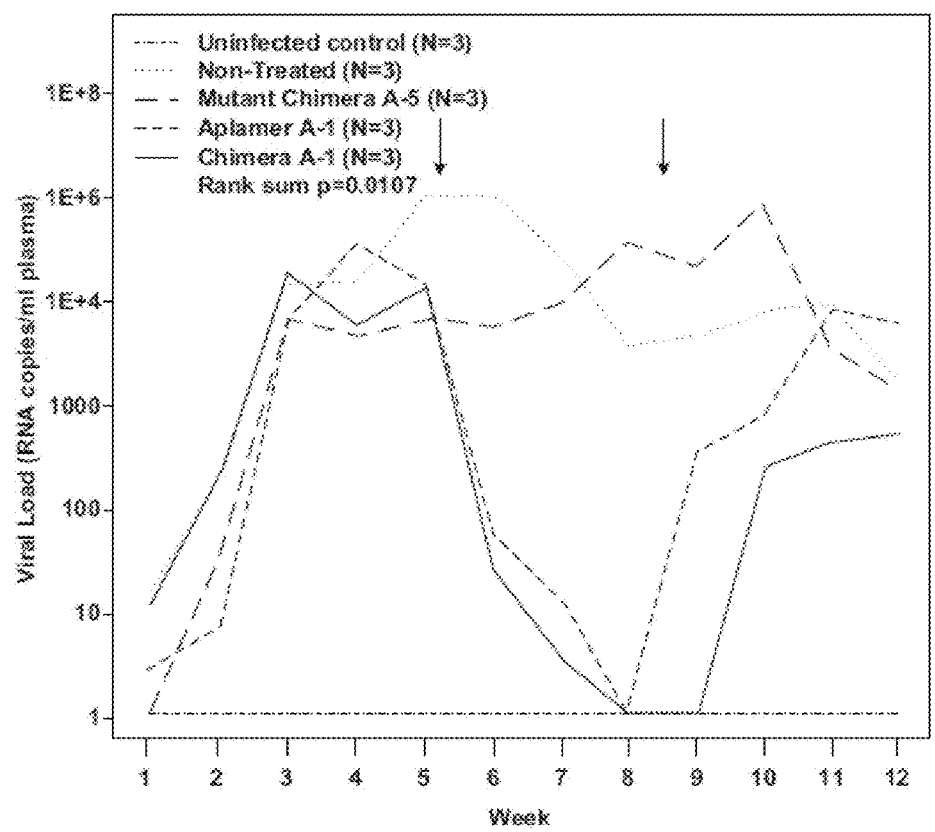

To determine the relative anti-HIV contribution of the siRNA component of the Ch A-1 aptamer-siRNA chimera, additional groups of 3 viremic animals were treated with 0.25 nmols of the A-1 aptamer, the chimeric Ch A-1 molecule and a mutant aptamer-tat/rev siRNA chimera Ch A-5. The A-5 aptamer portion of Ch A-5 has previously been shown to have poor affinity for gp120 [16]. Plasma viral loads were monitored to ascertain the efficacy of each treatment (FIG. 1B). Viral loads were strongly suppressed in A-1 and Ch A-1 treated mice compared to the nontreated group, reaching statistical significance (P=0.0107). No notable viral suppression was detected in the mice treated with the control, mutant aptamer-siRNA chimera Ch A-5 (FIG. 1B). The viral levels remained suppressed in all of the A-1 and Ch A-1 treated mice throughout the 3 week treatment period (weeks 6, 7- and 8). In the aptamer treated animals, there was viral suppression during the 3 week treatment period followed by moderate suppression continuing for an additional 2 weeks. In contrast, all of the Ch A-1 treated animals had undetectable viral loads at week 9, which is one week after the last injection (FIG. 1B). The lower viral loads in the Ch A-1 treated animals persisted through week 12. In contrast, viral loads returned to pre-treatment levels by week 11 in the animals treated with the A-1 aptamer alone. The enhanced duration of HIV-1 suppression afforded by the inclusion of the siRNA in Ch A-1 is statistically significant (p=0.04).

To validate that the Ch A-1 delivered the anti-tat/rev siRNA to infected T-lymphocytes, PBMCs were collected at one and three weeks during, and three weeks after the last treatment of the first set of animals. Small RNAs were extracted and analyzed for the presence of the tat/rev siRNA by real-time Taqman qRT-PCR assays. The results of these analyses showed that the tat/rev siRNA was detectable in PBMCs from all of the Ch A-1 treated mice at weeks five and seven, and in three of the animals at week 12, which is three weeks after the last injection (Data not presented). In contrast, no siRNAs were detected in the PBMCs of mice treated solely with tat/rev siRNA. Down-regulation of tat/rev gene expression was also assayed in PBMCs of infected and treated mice using qRT-PCR. Results showed a 75-90% reduction in the levels of tat/rev transcripts in chimera treated mice at both 1 and 3 weeks during the treatment period (data not shown).

Figure 2:
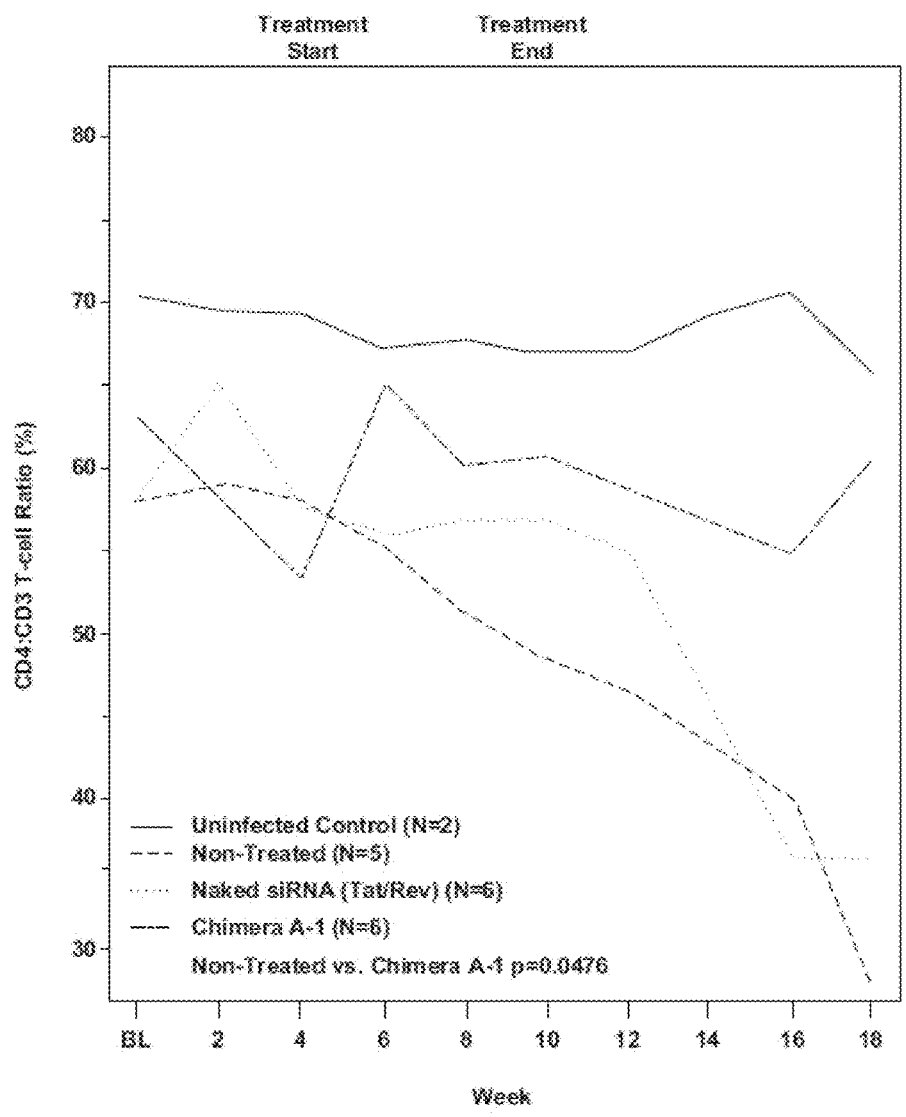
FIG. 2 illustrates that the Ch A-1 chimera protects RAG-hu mice from CD4 T-cell loss. CD4 T-cell levels were assessed by FACS at each indicated week pre- and postsiRNA treatment. Start and end of treatments are indicated by the yellow framed-in region. Uninfected mice (n=2), non-treated mice (n=5), naked tat/rev siRNA treated mice (n=6), anti-gp120 aptamer-tat/rev chimera (Ch A-1) treated mice (n=6) are indicated.

A major characteristic of HIV-1 infection is helper CD4+ T-cell loss during the acute stage of infection followed by a return to a set point for several months/years with an eventual depletion leading to AIDS [1, 24]. Therefore, prevention of CD4+ helper T-cell loss would contribute to immune reconstitution and restoration of immune function. To determine whether treatment of HIV-1 infected RAG-hu mice with the Ch A-1 chimera could protect against depletion of CD4+ T-cells, CD4+ T-cell levels were evaluated in peripheral blood collected at weekly intervals during and post treatment. The protection against T-cell depletion was significant when the non-treated group was compared with the chimera A-1 group (P=0.0476) (FIG. 2). In control, noninfected mice (HIV negative), the levels of CD4+ T-cells remained relatively stable within a 5% variation range, whereas in untreated HIV-1 infected mice the CD4+ T-cell levels began to decline beginning at 4 weeks post infection to below 50% of the starting levels at 18 weeks post-infection. In contrast, the levels of CD4+ T-cells in Ch A-1 treated mice remained at or near the levels of uninfected mice and this level remained stable well beyond the last treatment, indicating that the chimeric construct provides protection against CD4+ cell depletion.

In summary, in vivo testing of the anti-gp120 aptamer-siRNA chimera demonstrates potent inhibition of HIV-1 replication, functional delivery of the siRNA, and protection against HIV-1 mediated T-cell depletion. As shown in the Examples below, the anti-gp120 aptamer may be conjugated to an mRNA molecule to deliver backbone modified anti-SHIV encoding mRNAs to SHIV infected cells.

Example 2: Prevention of HIV (or SHIV) Infection by Genetically Modifying the CCR5 Gene with a Zn Finger Endonuclease Eradication of HIV-1 from infected individuals is a major challenge confronting scientists and physicians. The use of combinations of drugs in HAART has dramatically improved the course of infection in countries where the drugs are available, yet viral resistance and toxicities are still major problems. Once an individual stops taking his or her anti-retroviral drugs the virus rebounds rapidly. The examples described below use two different but complementary approaches to permanently eradicate viral replication by creating permanent mutations in the viral long terminal repeat (LTR) and CCR5 promoter via Zn finger endonuclease and homing endonuclease targeted cleavage and subsequent permanent mutational damage to the genomic DNA. As described below, the first approach involves the use of a gp120 aptamer while the second approach involves the use of a CD4 aptamer. One challenge of these approaches is effective delivery of the endonuclease encoding mRNAs or cDNAs to T-lymphocytes. It would be advantageous to deliver the nuclease coding sequences only to HIV-1 infected cells to avert off-target cleavage in non-infected cells.

Approach 1: gp120 Aptamer-mRNA Conjugates

The first approach, using an anti-envelope aptamer (e.g., gp120) has been shown to be feasible for delivery of functional dicer substrate RNAs to HIV-1 infected cells both in cell culture and in vivo in a humanized mouse model. This aptamer or any other aptamer which binds to and is internalized by a gp120+ cell (such as those described in Zhou, et al., *Selection, characterization and application of new RNA HIV gp 120 aptamers for facile delivery of Dicer substrate siRNAs into HIV infected cells*. Nucleic Acids Res, 2009. 37(9): p. 3094-109; which is hereby incorporated by reference as if fully set forth herein) may also be used to deliver backbone modified mRNAs to achieve targeted delivery of these mRNAs to SHIV infected cells. Thus, in some embodiments, the gp120 aptamer sequence is selected from:

```
A-1:
                                              (SEQ ID NO: 1)
5'-GGGAGGACGAUGCGGAAUUGAGGGACCACGCGCUGCUUGUUGUGA

UAAGCAGUUUGUCGUGAUGGCAGACGACUCGCCCGA-3'.

B-68:
                                              (SEQ ID NO: 2)
5'-GGGAGGACGAUGCGGACAUAGUAAUGACACGGAGGAUGGAGAAAA

AACAGCCAUCUCUUGACGGUCAGACGACUCGCCCGA-3'
```

The anti-gp120 approach has a dual function: anti-gp120 aptamer mediated neutralization of the SHIV strain and functional delivery of endonuclease encoding mRNAs into SHIV infected cells expressing the gp120 envelope on the cell surface. This envelope acts as a specific receptor for internalization of the aptamer and its cargo into cells [16].

Anti-gp120 aptamers [16] may be tested for their ability to neutralize a strain of SHIV (SHIV-11S7ipd3N4) [27]. The anti-gp120 aptamers have broad neutralizing capabilities with a variety of HIV isolates including Clade C (Neff et al., Sci Transl Med. 2011 Jan. 19; 3(66):66ra6; PMID 21248316). To test this two assays may be used. The first assay is to mix the functional or control mutant aptamers with the virus prior to infection of CEM T-cells as previously described and assay for blockage of infection [28]. The second assay involves infection of CEM T-cells with the SHIV strain followed by application of the aptamers to the culture medium. The anti-HIV activity of the aptamers will be monitored in all cases by monitoring the production of infectious SHIV using both quantification of the viral secreted gag antigen as described previously [29-30]. Additional aptamers derived from previous studies may also be tested. The aptamers are transcribed from DNA templates using a modified T-7 RNA polymerase and 2' Fluoro modified pyrimidine NTPs and 2' OH ribose purine NTPs. The 2' Fluoro backbone stabilizes the aptamer against serum ribonuclease degradation. If the aptamers do not have strong antiSHIV activity, additional aptamers may be generated and selected using a SELEX process using SH IV strain as a target. More specifically, a cell based SELEX incorporating using SHIV infected CEM T-cells may be used to identify aptamers against SHIV.

The SELEX procedure involves toggling of the library by first binding of the aptamer library to non-infected CEM T-cells to select out those RNAs that are binding to non-viral cell surface proteins. The remaining library members are then used to treat SHIV infected cells. Aptamers are allowed to bind for six hours to ensure internalization takes place. RNAs that are on the surface will be removed by protease treatment and RNAse T1, which cleaves at unmodified guanosines. The internalized aptamers may be isolated by fractionation of the cell cytoplasm and reverse transcribing the library as previously described [16]. The process of transcription, binding, isolation and reverse transcription is repeated for several rounds. The candidates may be analyzed by Solexa deep sequencing of the library beginning at the sixth round, looking for enriched families of sequences. If there is a substantial enrichment of a particular motif, the DNA encoding the aptamers may be chemically synthesized, and purified preparations of individual aptamers may be transcribed in vitro and tested for inhibition of SHIV infection and internalization using Cy3 and confocal microscopy as previously described [16, 28]. Libraries containing 50 randomized bases between the unique sequence primers have been used previously. However, since this process may ultimately generate a large RNA molecule, the use of smaller libraries containing 20 and 30 randomized bases may be tested to aid in the future chemical synthesis of the aptamers for in vivo testing. Once the aptamers which effectively neutralize the SHIV strain and are internalized in SHIV infected cells have been established, they will be chemically synthesized with a 3' linker sequence described by Zhou et al [16]. This "sticky bridge" sequence will allow us to attach, in vitro, transcribed mRNAs which have a complementary bridge sequence to the aptamers as described in the above reference for siRNAs. The mRNAs may be transcribed using the new procedure recently described for biochemically synthesizing mRNAs used for the programming of induced pluripotent stem cells [31]. The mRNAs described in [31] have been backbone modified to block activation of TIRs and are actively translated. 2' FI pyridine NTPs may also be incorporated into the in vitro transcribed mRNAs to enhance stability in serum and in cells.

Figure 7:
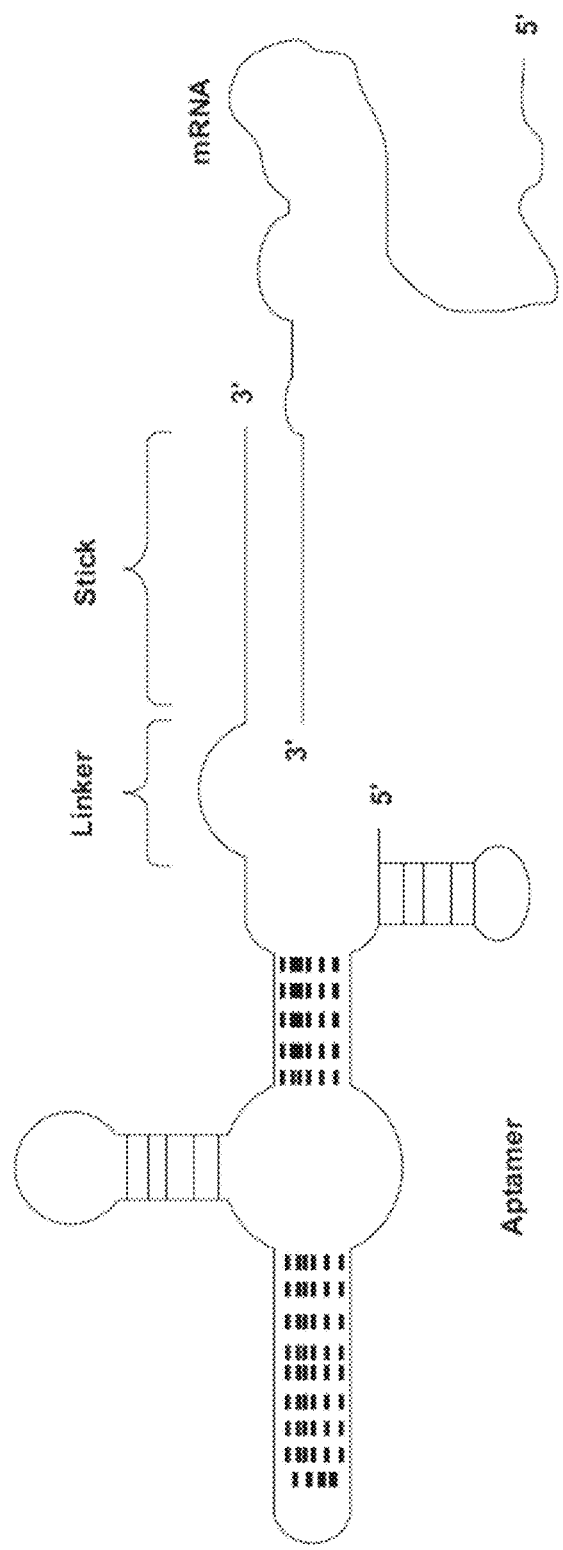
FIG. 7 is a schematic diagram of an aptamer-stick-mRNA hybrid. This strategy was used for inserting siRNAs via complementary base pairing to the GC rich stick, the siRNAs were functionally delivered to HIV-1 infected cells via this approach (Zhou et al. 2009).

The method for annealing the mRNA to the aptamer is shown below in FIG. 7. The bridge sequence will be appended to the 3' end of the mRNA, allowing the use of a cap on the 5' end. The first test of this approach will take advantage of eGFP mRNAs. eGFP mRNAs may be synthesized using the in vitro transcription approach and anneal these to the "sticky bridge" of the aptamer. These will be delivered to SHIV infected cells and assayed for eGFP expression as described below.

Figure 8:
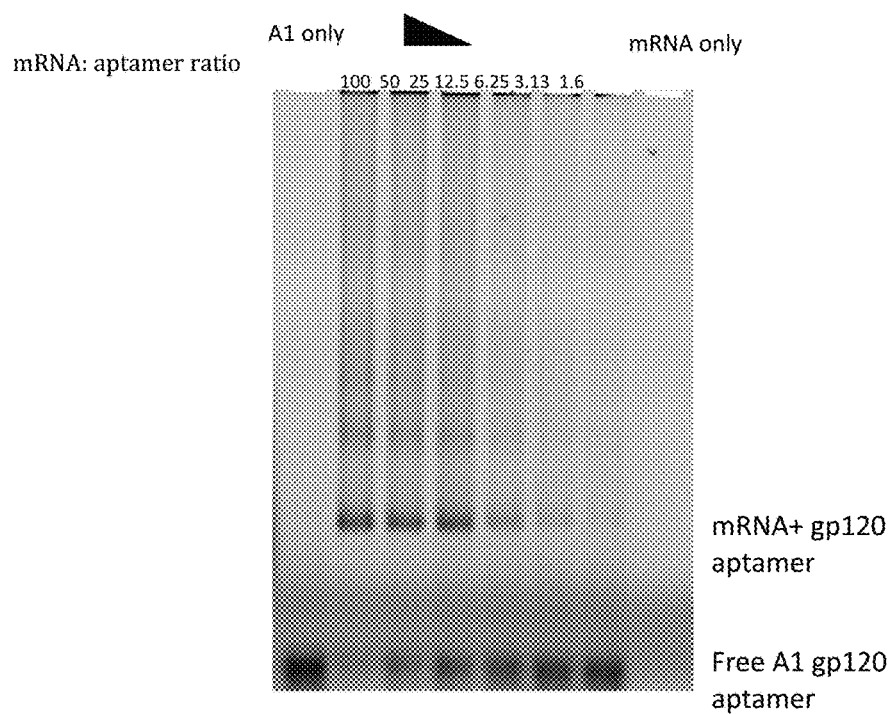
FIG. 8 shows results of a gel shift assay illustrating that the gp120 aptamer dimerizes with eGFP encoding mRNA according to one embodiment.
Figure 9:
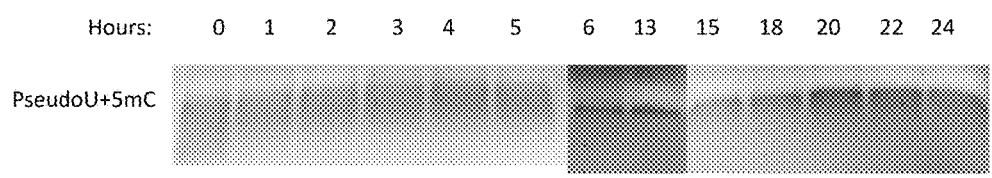
FIG. 9 is a gel illustrating that illustrates that gp120 aptamer-mRNA conjugates (or complexes) are stable after incubation at 37° C. in 10% human serum for over 24 hours.

Briefly, the gp120 aptamer was labeled with Cy3 and incubated with eGFP mRNA for 20 minutes at room temperature. The complexes formed were leaded on a native agarose gel and imaged using a typhoon imager. As shown in FIG. 8, the gp120 aptamer dimerized with eGFP mRNA to form a gp120 aptamer-eGFP mRNA conjugate. These gp120 aptamer-eGFP mRNA conjugates formed were determined to be stable complexes (FIG. 9).

Figure 10A:
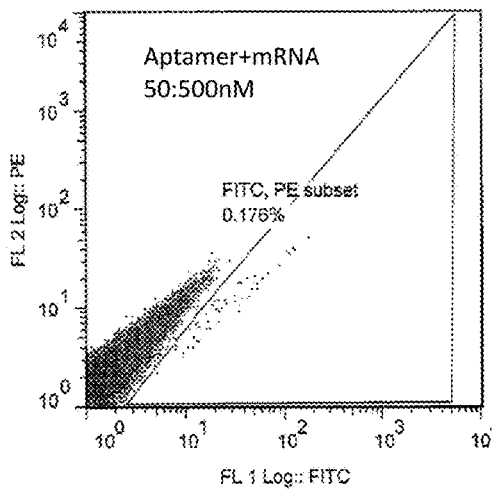
FIGS. 10A-10C show FACS analysis results illustrating low levels of eGFP protein expression in CHO-gp160 cells incubated with gp120 aptamer-eGFP mRNA conjugates (Aptamer+mRNA) at a ratio of 50:500 nM (FIG. 10A). eGFP protein expression was not observed in CHO-gp160 cells incubated with the Aptamer only or the mRNA only (FIG. 10B, FIG. 10C).
Figure 10B:
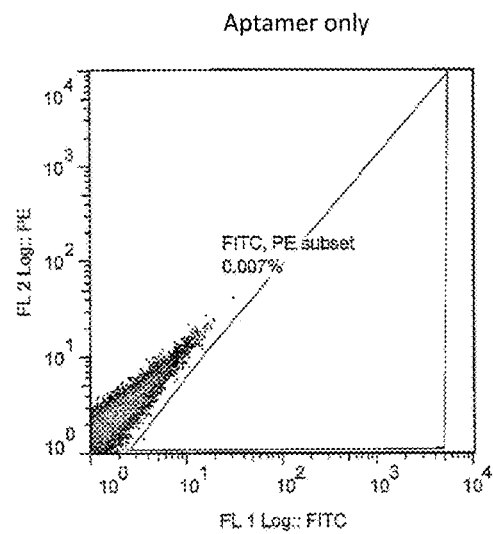
Figure 10C:
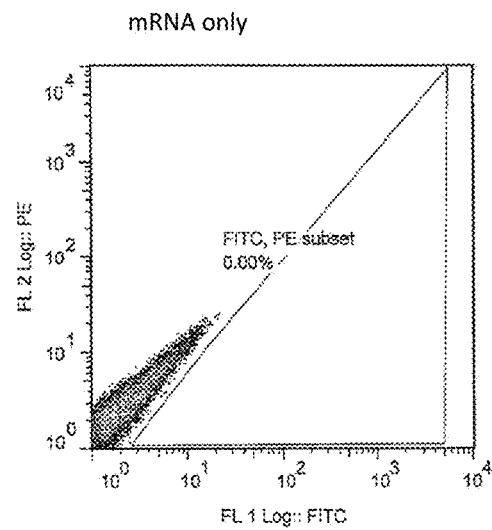

The gp120 aptamer-eGFP mRNA conjugates were added to the cell culture medium of CHO-gp160 cells at a ratio of 50:500 nM, resulting in low eGFP protein expression in the cells (FIG. 10A). eGFP protein expression was not observed in CHO-gp160 cells incubated with the Aptamer only or the mRNA only (FIGS. 10B and 10C).

Figure 11:
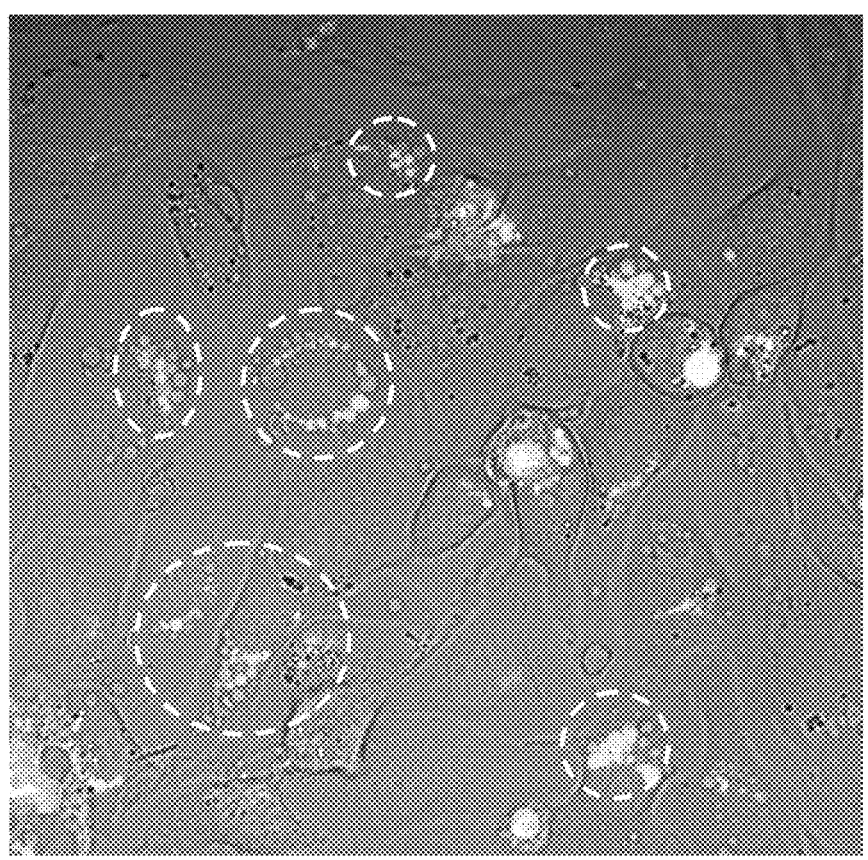
FIG. 11 illustrates eGFP mRNA localization in small vesicles within CHO-gp160 cells. Cy5 labeled mRNA indicated by dashed circles.
Figure 12:
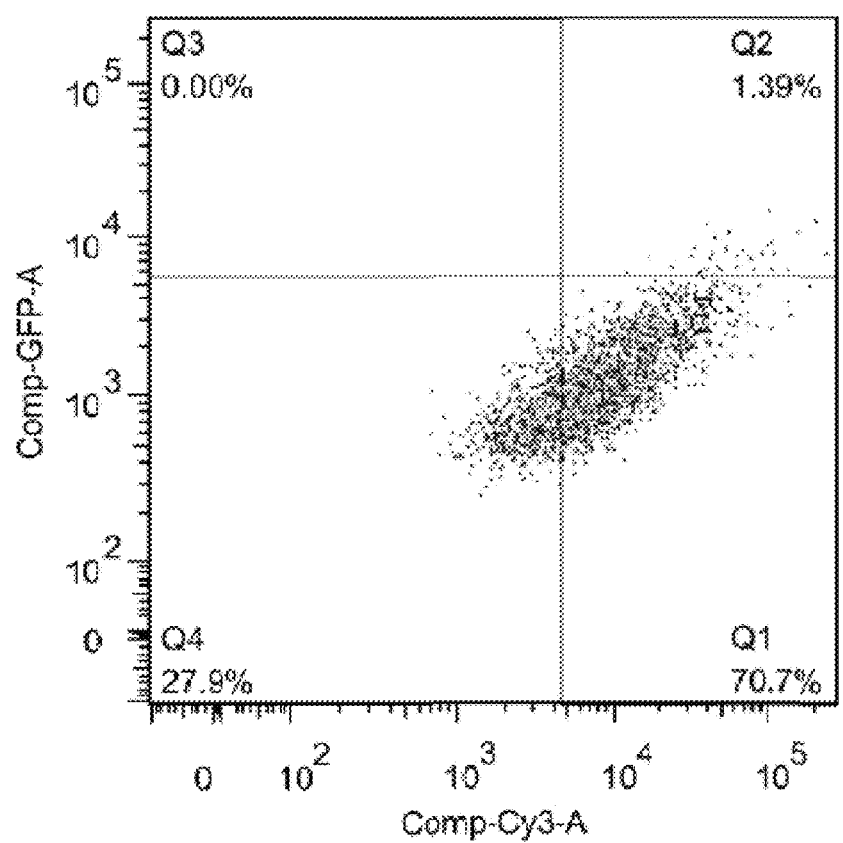
FIG. 12 shows FACS analysis results illustrating that Cy3 labeled eGFP mRNA is delivered to CHO-gp160 cells when hybridized to gp120 aptamer.
Figure 13:
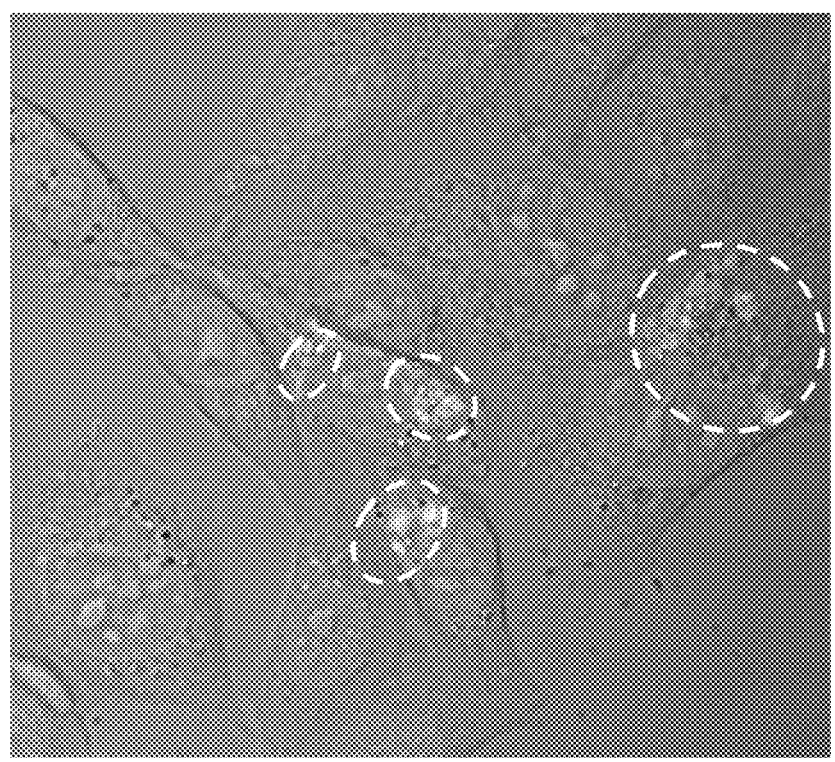
FIG. 13 illustrates that gp120 aptamer-eGFP mRNA conjugates colocalize within cells after delivery. The Aptamer was labeled covalently with Cy3 (red), while eGFP mRNA appears green (both are indicated by dashed circles in figure). The complexes (or conjugates) were formed prior to addition to the culture medium and were assayed 24 hours after addition.
Figure 14A:
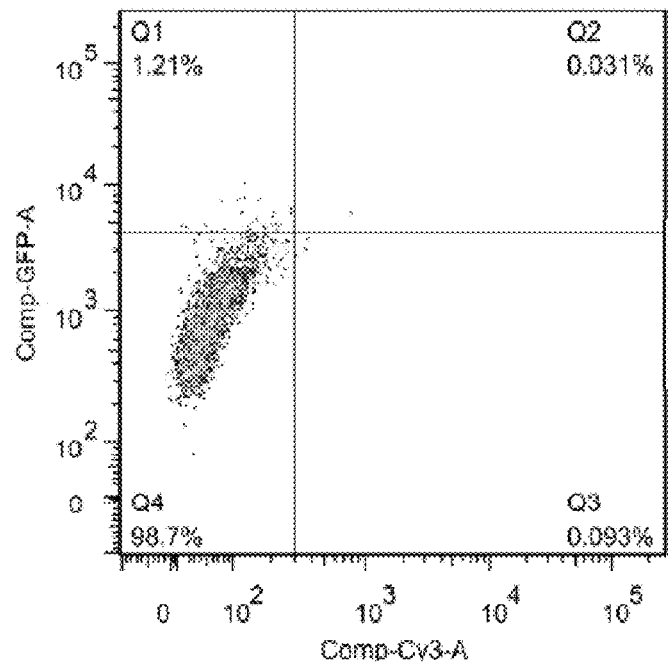
FIGS. 14A-B show FACS analysis results (FIG. 14A) and a fluorescence image (FIG. 14B) of eGFP protein expression (indicated by dashed circles in Figure HB) in CHO-160 cells after aptamer mediated delivery. Cells were analyzed 24 hours after addition of gp120 aptamer-eGFP mRNA conjugates.
Figure 14B:
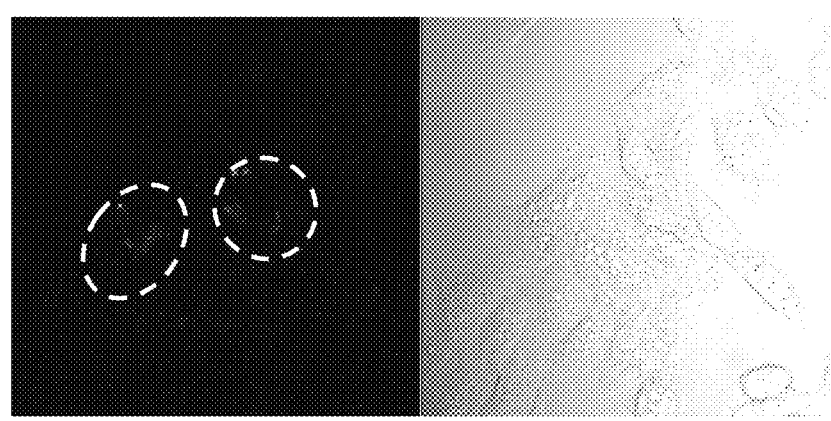
Figure 15:
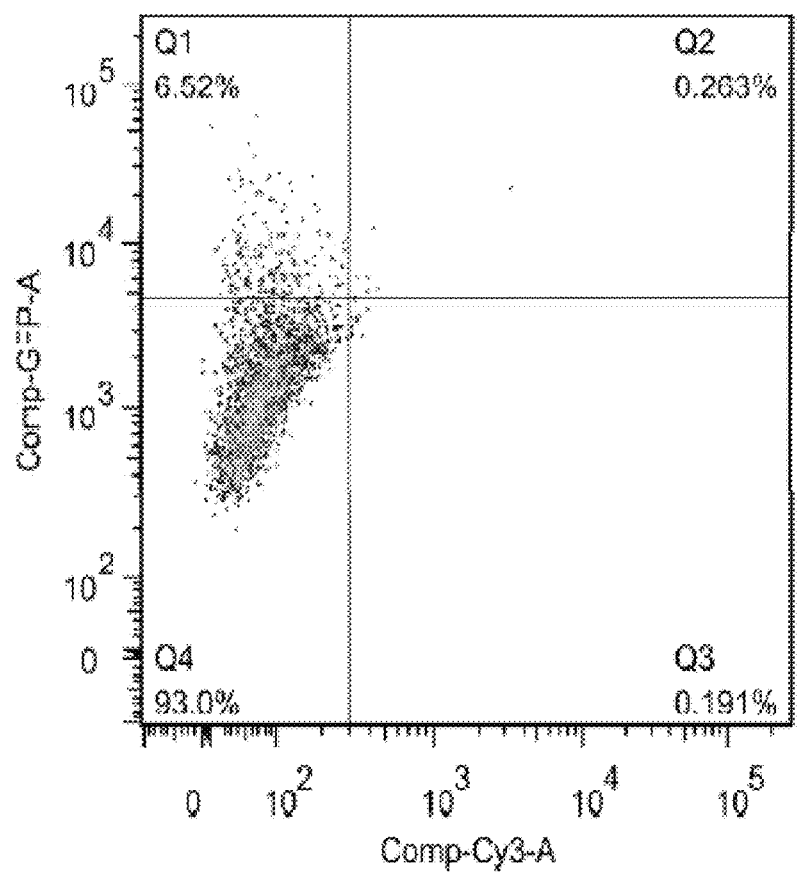
FIG. 15 shows FACS analysis results of adding Chloroquine to CHO-gp160 cells in conjunction with the gp120 aptamer-eGFP mRNA conjugates. Chloroquine addition increases the level of eGFP expression as compared to addition of the conjugates alone. Cells were analyzed 24 hours after addition of the conjugate.
Figure 16:
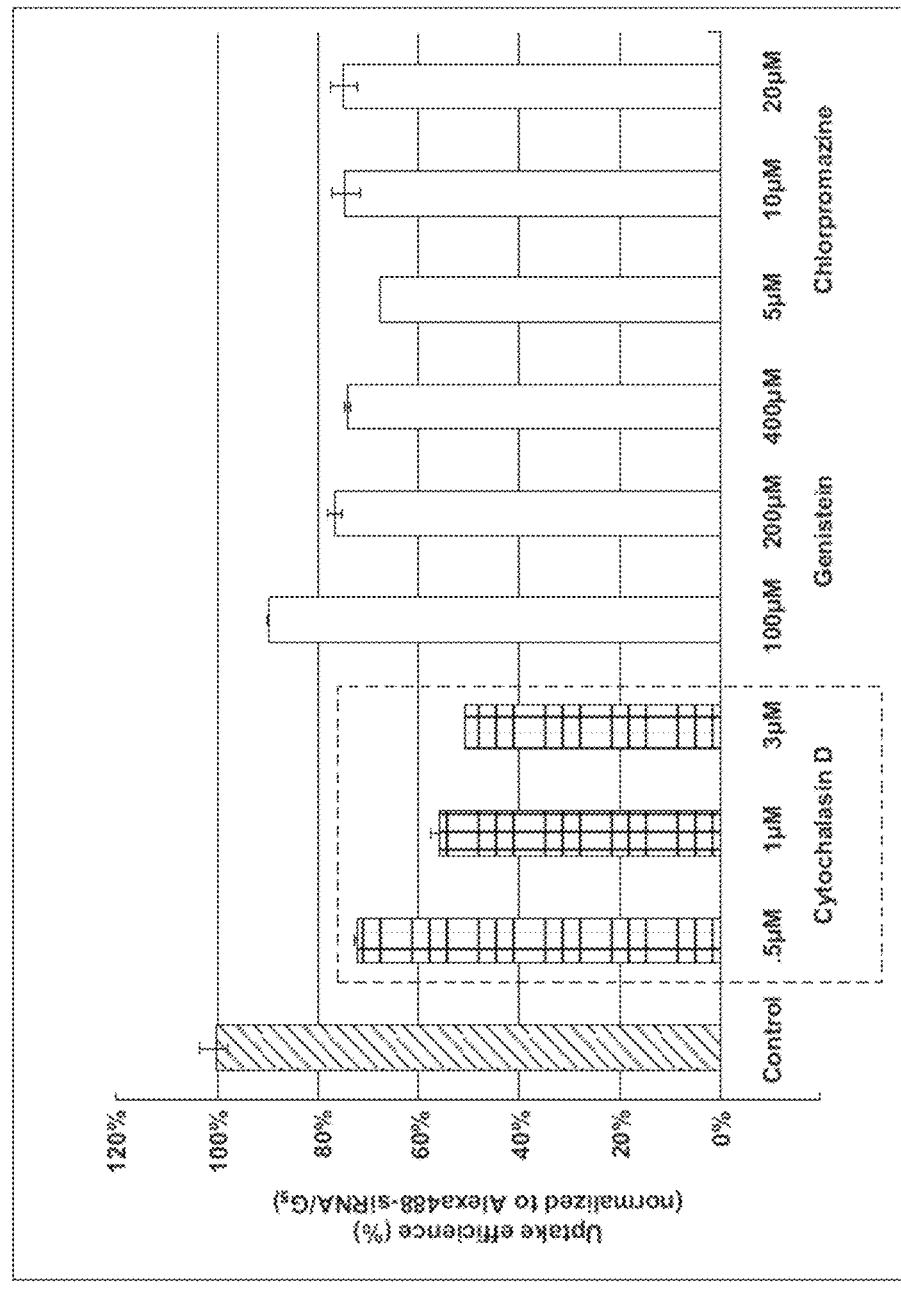
FIG. 16 illustrates cell uptake pathways using different uptake inhibitors. Macropinocytosis is the dominative cell uptake pathway.

Cy5 labeled mRNA hybridized to Cy3 labeled gp120 aptamer (i.e., labeled gp120 aptamer-eGFP mRNA conjugates) was added to CHO-gp160 cells to confirm that the aptamer and mRNA are internalized by the cells. FIG. 11 illustrates that the mRNA localizes in small vesicles within the cells after 12 hours. FACS analyses also confirms that Cy3 labeled eGFP is delivered to CHO-gp160 cells when hybridized to the gp120 aptamer (FIG. 12). After delivery, the labeled gp120 aptamer-eGFP mRNA conjugates colocalize within the CHO-gp160 cells (FIG. 13). Further, CHO-gp160 cells express low levels of eGFP after 24 hours (FIG. 14). To increase expression levels of eGFP mRNA, Chloroquine was added in conjunction with the labeled gp120 aptamer-eGFP mRNA conjugate (FIG. 15). These results indicate that the gp120 aptamer-eGFP mRNA conjugates described herein are able to target cells expressing gp120 and deliver a desired mRNA molecule for intracellular expression in the target cell. Based on these results, one skilled in the art would understand that conjugates using any aptamer to target a surface molecule on a desired target cell may be conjugated to any desired mRNA molecule for its expression in the target cell. An additional example targeting BAFF-R is discussed below.

In another embodiment, the aptamer and mRNA may be co-transcribed, but may include an IRES element in the mRNA to allow internal translational initiation. There are several possible IRES elements which are commonly used for this purpose, so different sequences may be tested to obtain the one that functions most optimally in these aptamer fusions.

Because the backbone modified eGFP mRNA can be functionally expressed from the complex or conjugate, sequences encoding the Zn finger nuclease and homing endonucleases may be synthesized and conjugated to the aptamer. These conjugates may be delivered to SHIV infected cells and assayed for nuclease mediated targeting of the SHIV genome via PCR amplification and sequence analyses. As described for eGFP the mRNA may be produced via in vitro transcription since the length of the mRNAs precludes current mRNA synthesis technologies. Large scale transcription is not a problem, though, and the in vitro transcribed mRNA will be annealed to the linker as shown in FIG. 7.

Approach 2: CD4 Aptamer-mRNA Conjugates

The second approach takes advantage of a previously published CD4 specific aptamer to deliver a Zn finger nuclease encoding mRNA to uninfected CD4+ cells for inactivation of the CCR5 co-receptor gene. The aptamer delivery approach could set the stage for targeted delivery of a host of other therapeutic mRNAs into HIV-1 infected cells and ultimately result in purging of these cells from patients.

Further, an aptamer that targets CD4 and is internalized [26] may be used for cell type specific delivery of a CCR5 Zn finger endonuclease encoding mRNA to PBMCs. The same approach as described above for the gp120 aptamer may be adapted for the CD4 aptamer, which incorporates a "sticky bridge" sequence for annealing the in vitro transcribed mRNA to the aptamer. As described above, this aptamer will be tested for delivery of an eGFP mRNA into CEM T-cells, and when successful, into PBMCs. Zn finger endonuclease mRNA targeting CCR5 will be transcribed in vitro and annealed with the CD4 targeting aptamer.

In order to assay for disruption of CCR5, PBMCs may be used. The functional production of the endonuclease will be monitored by PCR amplification of the CCR5 targeted region followed by DNA sequence-analyses. To determine the effectiveness of the modification the M-tropic HIV isolate BaL may be used to infect PBMCs with or without prior treatment with the aptamer-endonuclease fusion and monitor viral p24 production. Those cells that have been successfully modified with the Zn finger endonuclease (either one or both alleles) should have a selective growth advantage and the percent of CCR5 modified cells should increase relative to unmodified cells. DNA may be isolated before and after the viral challenge and carry out Southern blot analyses to detect the relative proportions of gene modified versus unmodified genomes. The gene modified population should be increased relative to the unmodified population. The dosing of aptamer-mRNA will be optimized until the maximal amount of modification is reached. Finally, possible off target cleavage events will be monitored as a function of aptamer-mRNA dosing.

Example 3: PAMAM Dendrimers for the In Vivo Delivery of Anti-HIV Zn Finger and Homing Endonuclease cDNAs or mRNAs to CD4+ Lymphocytes Because PAMAM flexible cationic dendrimers can be rapidly synthesized and have been successfully used for in vivo delivery of siRNAs, the same strategy may be used for delivery of mRNAs with or without associated aptamers.

Figure 3:
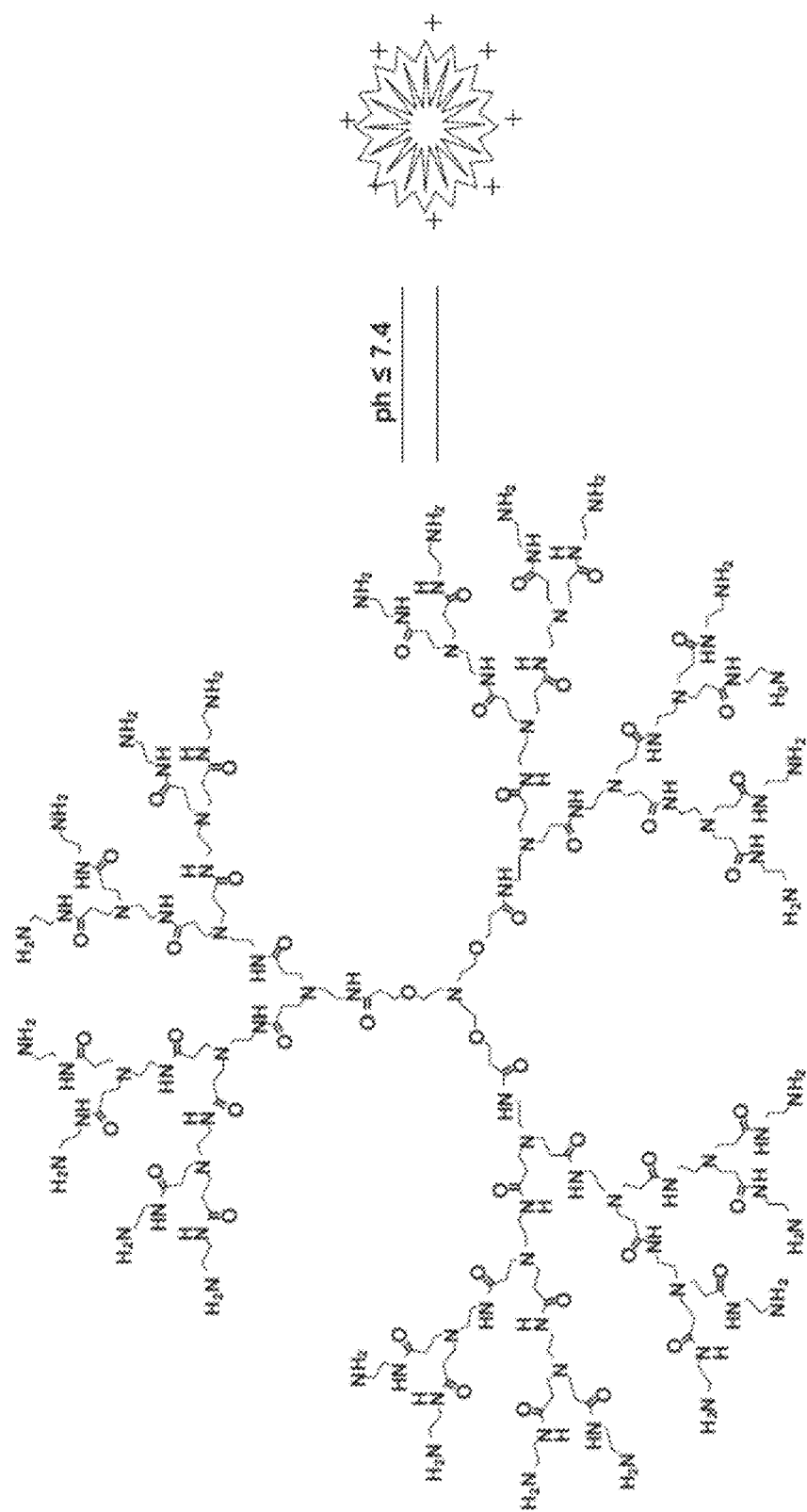
FIG. 3 illustrates Flexible PAMAM dendrimers with a triethanolamine core ($G_3$ dendrimer as an example).
Figure 4:
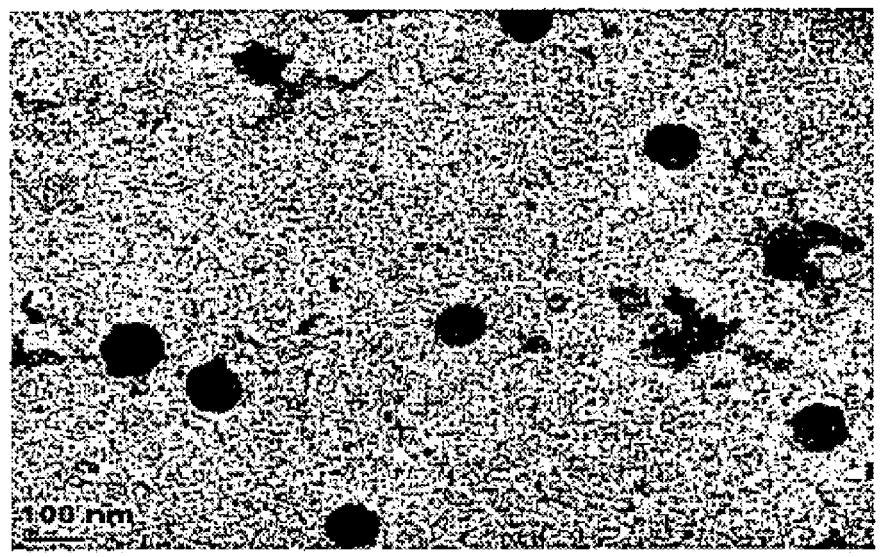
FIG. 4 is a TEM image of G5-dsiRNA nanoparticles
Figure 5:
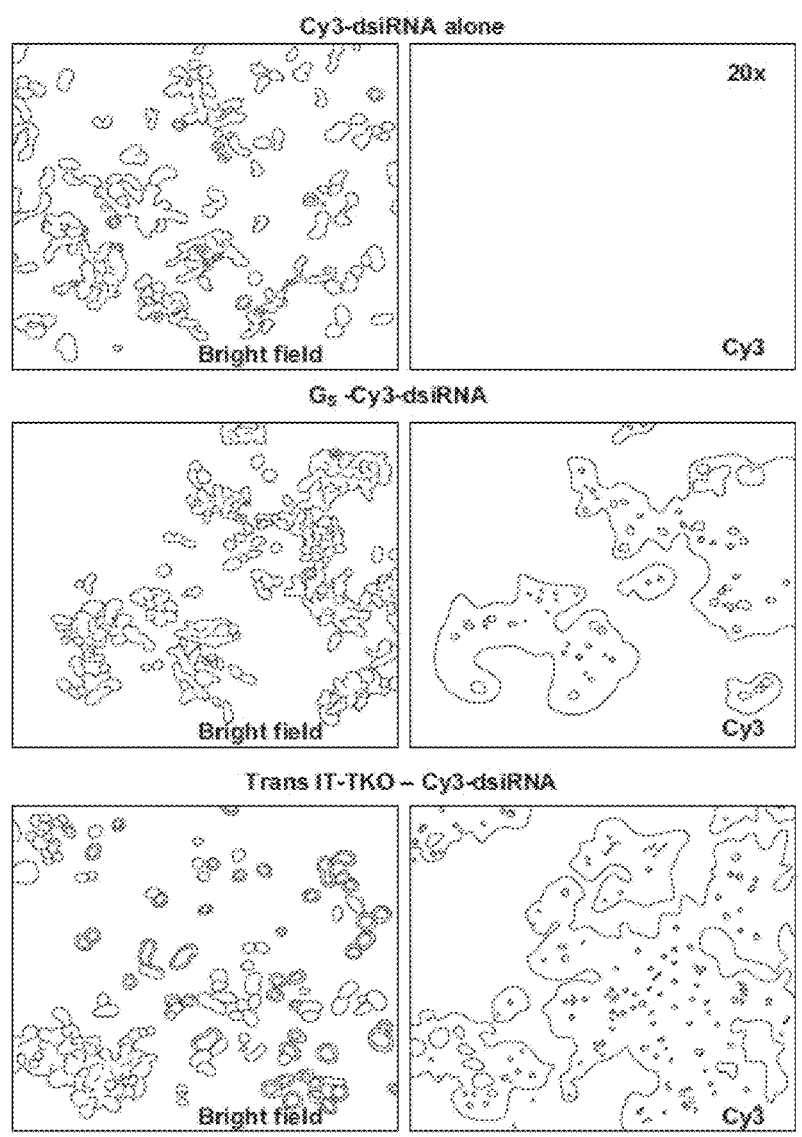
FIG. 5 is a set of exemplar images illustrating cellular uptake of G5-dsiRNA complexes in CEM T-cells

The basic dendrimer structure is shown in FIG. 3. The dendrimers have a net positive charge to allow complexes with siRNAs and other nucleic acids. The dendrimer-siRNA complex forms 100 nM particles (FIG. 3) and the particles have been used to deliver anti-HIV siRNAs to T-lymphocytes in vitro (FIG. 4) and in vivo as discussed below. It was found that the generation 5 (G5) dendrimers gave effective siRNA delivery to T-cells (FIG. 5).

Figure 6:
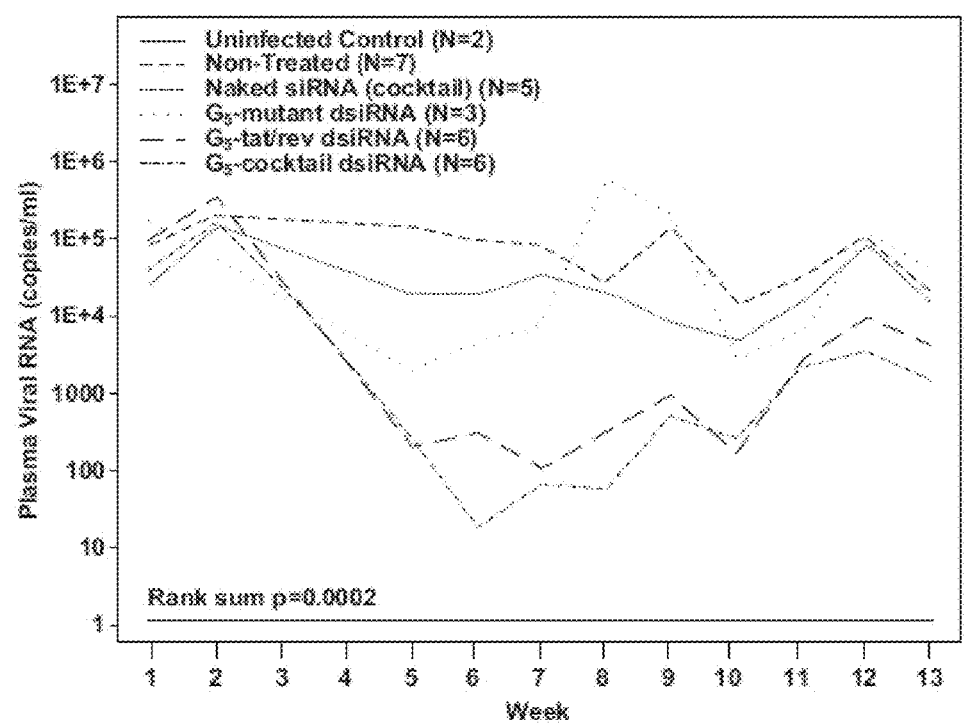
FIG. 6 shows that systemic administration of dendrimer-siRNA complexes suppresses HIV-1 viral load in vivo. Ten micrograms of siRNAs were complexed with the G5 dendrimer and tail vein injected once per week into HIV-1 infected humanized mice. The arrows indicate the beginning and end of the injection period.

This G5 dendrimer has been tested for functional delivery of anti-HIV siRNAs both in cell culture and in vivo. The in vivo application involved delivering either a single siRNA targeting HIV-tatlrev or a cocktail of siRNAs targeting HIV-1 tat/rev and cellular CD4 and TNP03 targets. The results presented in FIG. 6 demonstrate effective inhibition of HIV-1 replication in a humanized mouse model. Therefore, according to some embodiments, PAMAM dendrimers may be used to deliver Zn finger nuclease and homing endonuclease mRNAs or cDNAs to CEM T-cells and rhesus PBMCs. The PAMAM dendrimers have been shown to be effective in the delivery of cDNAs and now siRNAs. In some aspects, the PAMAMs may be used to deliver both mRNAs and cDNAs encoding the site specific cleaving Zn finger and homing endonucleases. It is important to note that in addition to siRNA delivery, PAMAM dendrimers have been shown to be effective in cDNA delivery [25].

Several generation variants of the PAMAM dendrimers may be synthesized and tested. The PAMAM dendrimers will be synthesized as previously described [32-33]. The various dendrimer generations from G3 through G7 may be tested for their ability to package the in vitro transcribed mRNAs described in Aim 1. As a first test, the eGFP mRNA will be used to test for effective cytosolic delivery and expression of into functional eGFP protein. Various N:P ratios of dendrimers to mRNA or cDNA may be tested to obtain the most effective ratio for complex formation and delivery to CEM cells and PBMCs. Once the optimal dendrimer generation and N:P ratio is determined, testing will be switched to the Zn finger endonuclease and homing endonuclease mRNAs, CEM T-cells and ultimately in PBMCs. Assays for Zn finger nuclease disruption of the CCR5 gene will be carried out as described above.

Additionally, PAMAM dendrimer mediated delivery of cDNAs to CEM T-cells, lymphocytes and PBMCs may be used. It is important to evaluate the relative efficacy of nuclease mediated mutational perturbation of the SHIV DNA when the nucleases are expressed from the backbone modified mRNAs versus cDNAs. For the cDNAs the use of various promoters that have been shown to be effective in lentiviral vectors used for gene expression in macaque cells will be analyzed [30]. The primary assay for testing expression of the nucleases will be Northern gel analyses of RNAs from cells treated with the dendrimers-cDNAs. If these analyses demonstrate mRNA production, the functional consequences of nuclease modification of the CCR5 promoter or integrated SH IV sequences will be monitored using PCR amplification of the targeted DNA followed by DNA sequence analyses. To quantify the effects and extent of genomic modification SHIV replication may be monitored using standard assays to monitor viral replication in cultured cells [30].

The mechanism of PAMAM dendrimer uptake has been previously studied. From FIG. 16 it can be seen that for siRNAs, the mechanism appears to be macropinocytosic, since Cytochalasin 0 inhibits siRNA delivery. To better understand the mechanism of dendrimer mediated delivery of the mRNAs or cDNAs this panel of inhibitors will also be tested for inhibition of uptake of the control eGFP mRNA and/or cDNA in GEM T-lymphocytes and PBMGs.

To determine the optimal dendrimer:mRNA or cDNA ratio for gene expression the dendrimers will be titrated with increasing amounts of eGFP mRNA or cDNA and deliver the complexes to GEM T-cells and ultimately PBMGs. FACS analyses may be used to quantify eGFP expression as a function of concentration of the mRNA or cDNA. When the optimal ratio is determined these will be tested for delivery of Zn finger and homing endonuclease encoding mRNAs or cDNAs in uninfected or SHIV infected GEM T-cells. The efficiency of SHIV silencing in infected cells will be determined by conventional gag antigen production and reduction in viral RNAs using qRT-PGR assays. For endonuclease disruption of the SHIV genomes it may be more appropriate to use SHIV gag antigen and viral RNA production as a measure of the efficacy of the nucleases as opposed to monitoring the frequency of mutations by PGR since each infected cell will have variable numbers of integrated viral DNA copies.

In summary, PAMAM flexible dendrimers have been tested for the in vivo delivery of anti-HIV siRNAs and show no toxicity, allow functional delivery of siRNAs into primary human PBMCs and cause inhibition of HIV replication. The PAMAMs may also be used for delivery of modified mRNAs and/or cDNAs encoding endonucleases targeting CCR5 and the SHIV genome.

Example 4: BAFF Aptamer Mediated Delivery of Synthetically Modified mRNA

Delivery of mRNA to target cells by an aptamer is not limited to a particular cell, and the therapeutic effects are not limited to the treatment of HIV described in the Examples above. For example, B cell lymphoma may be treated using BAFF-R aptamers conjugated to mRNA molecules as discussed below.

Based on the finding that pseudouridine and 5-methylcytidine within mRNA reduces immune activation, mRNA was analyzed as a candidate for gene therapy. Since cell specificity is important to reduce side effects, mRNA conjugated to the BAFF-R aptamer may be an effective therapy for the treatment of B cell lymphoma. Successful dimerization of eGFP and the BAFF R-1 aptamer was achieved. Furthermore, this complex remained able to bind to BAFF-R protein. The aptamer mediated entry of the mRNA followed by expression. Based on these findings, other mRNAs may be synthesized for aptamer based delivery.

The natural ligand for this receptor is the Baff protein. Binding of Baff to the receptor results in increased B cell proliferation and survival (34). The BAFF receptor (BAFF-R) may be used as a target for selective therapeutic delivery of siRNAs and other growth inhibitory agents to B-cells lymphomas for the therapeutic treatment of this disease.

Previous studies have demonstrated that a BAFF-R1 aptamer can functionally deliver siRNAs into B-cells expressing the BAFF receptor. The siRNAs have been shown to be released from the aptamer and function in the RNAi pathway. Based on the success of the selective delivery of siRNAs to BAFFR expressing cells, the aptamer may be tested for selective delivery of base and backbone modified messenger RNAs into B-cells. This allows for the aptamer to selectively deliver mRNAs encoding cytotoxic peptides or proteins to B-cell lymphomas as part of a therapeutic treatment for this disease.

The base and backbone modifications of mRNAs include replacing U and C residues with pseudouridine and 5-methylcytidine. Addition of a 5' cap and removal of phosphate groups add to the modifications. The purpose of these modifications is to prevent immune activation by the RIG-1 pathway. Previous synthesis of modified mRNAs resulted in dramatically decreased immune activation when compared to unmodified RNA resulting in decreased cell cytotoxicity (35, 36).

Aptamers may be used to deliver modified mRNA to cells in a receptor mediated manner. The BAFFR aptamer conjugated to this mRNA allows for delivery in a liposome independent manner. The transient expression achieved is useful because treatment can be regulated by withdrawing or adding the amount of transcripts treated with.

Aptamer Mediated mRNA Delivery Approaches BAFF-R RNA aptamer may be dimerized with an mRNA encoding eGFP to test the concept that an aptamer can deliver mRNAs to cells via receptor mediated endocytosis.

Figure 18:
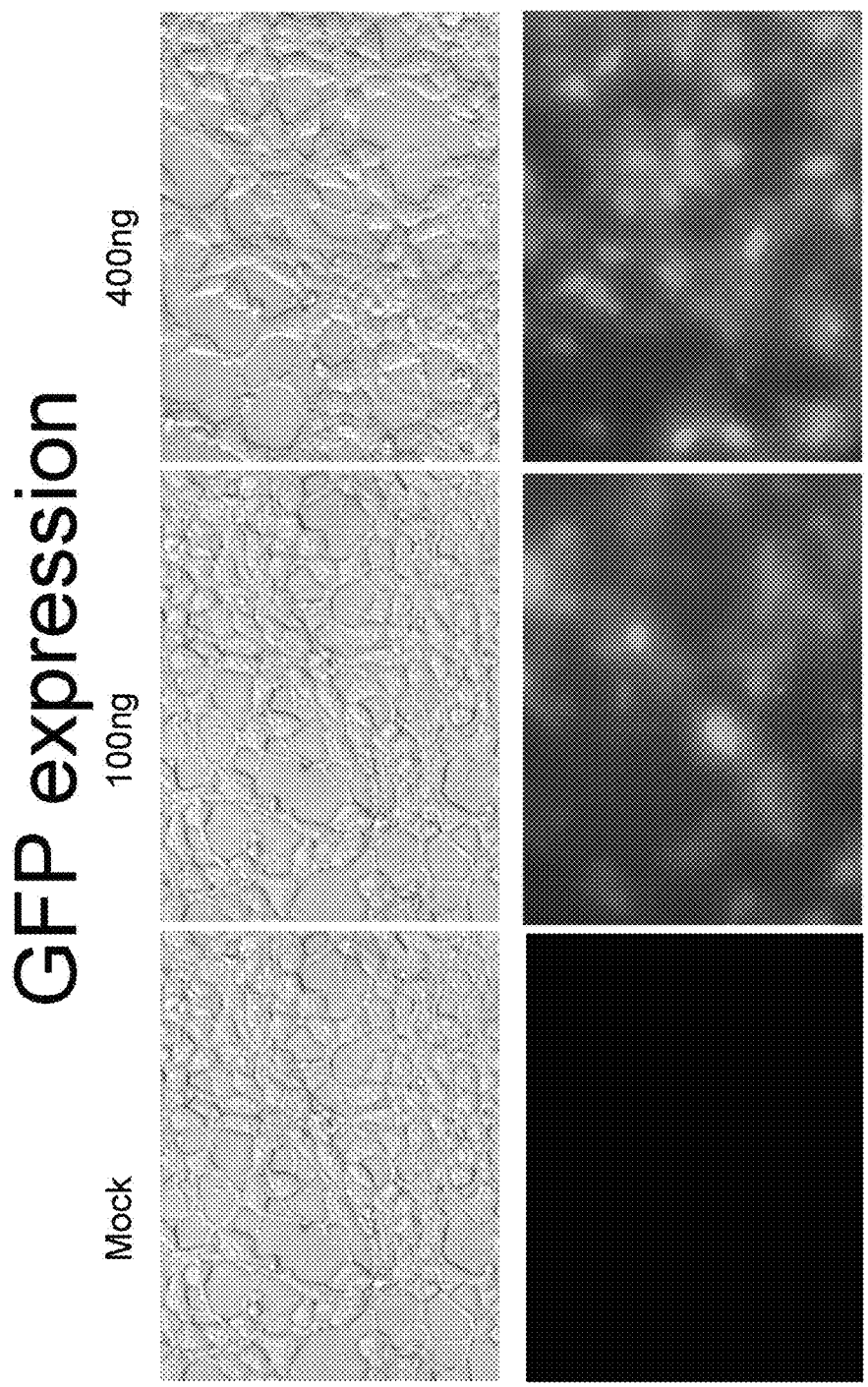
FIG. 18 illustrates that the modified synthetic mRNA can be effectively translated in HEK293 cells following transfection.

To conjugate the mRNA to the R-1 aptamer (FIG. 17), a complementary stick sequence was added to the mRNA so it could base pair with the complement appended to the aptamer. The stick on the mRNA is downstream of the poly A tail. The poly-A tail contained 120 A residues to enhance translation and stability of the mRNA. The 5' and 3' UTRs along with the 5' cap also enhance the stability and translation efficiency of the mRNA. The aptamer is heavily backbone modified with 2' FI while the mRNA has both base and backbone modifications. Backbone modifications within the mRNA include the replacement of cytidine and uridine residues with 5'm cytidine and pseudouridine along with removal of 5' phosphate groups by Antarctic phosphatase (35). The in vitro transcribed eGFP mRNA was transfected into HEK293 cells using RNAiMax to determine whether the mRNA would be translated in the cells. The modified synthetic mRNA was shown to be effectively translated in HEK293 cells following transfection (FIG. 18).

Figure 19:
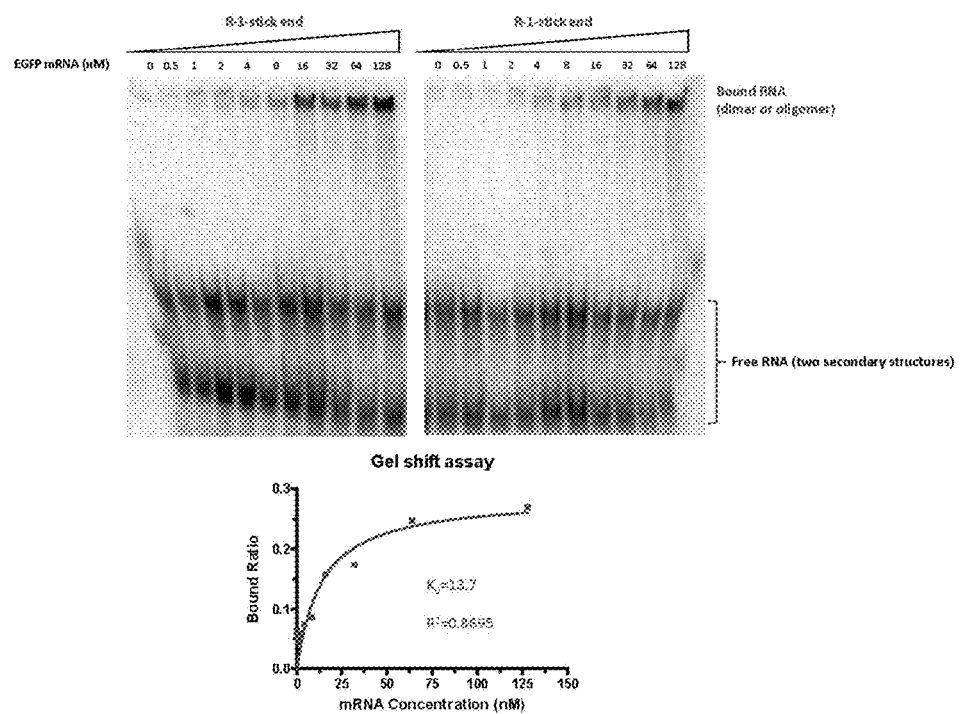
FIG. 19 shows that the stick sequence on the mRNA forms a stable complementary base pair with the stick on the aptamer.

Radioactively labeled R-1 BAFF aptamer was incubated with eGFP mRNA. After incubation, the products were separated on a native PAGE gel. Observable complexes were observed at the top of the gel. Since the size of the mRNA is 1059 bp, it takes much longer to migrate through the gel. The two bottom bands are different conformations of unbound aptamer. Aptamer levels were constant while mRNA concentration was varied (FIG. 19).

Figure 20:
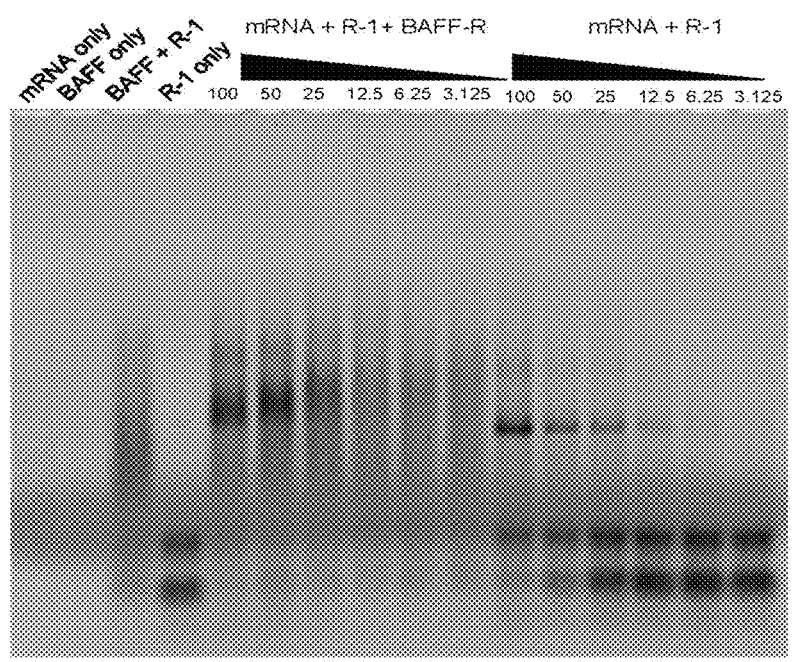
FIG. 20 shows a native PAGE gel that illustrates shows an R-1 aptamer fluorescently labeled with Cy3 dimerized with eGFP mRNA and bound to BAFF-R protein.
Figure 20:
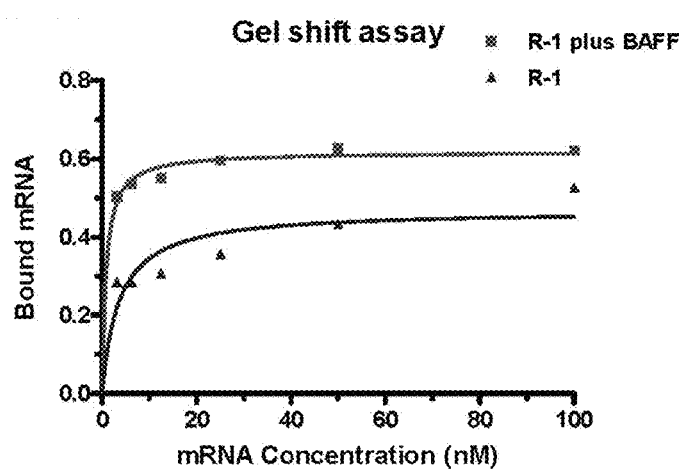

The R-1 aptamer was dimerized to the eGFP mRNA. The complexes formed were then incubated with BAFF-receptor. The concentration of the mRNA was varied, but R-1 and BAFF-R protein levels were held constant (FIG. 20).

Figure 21:
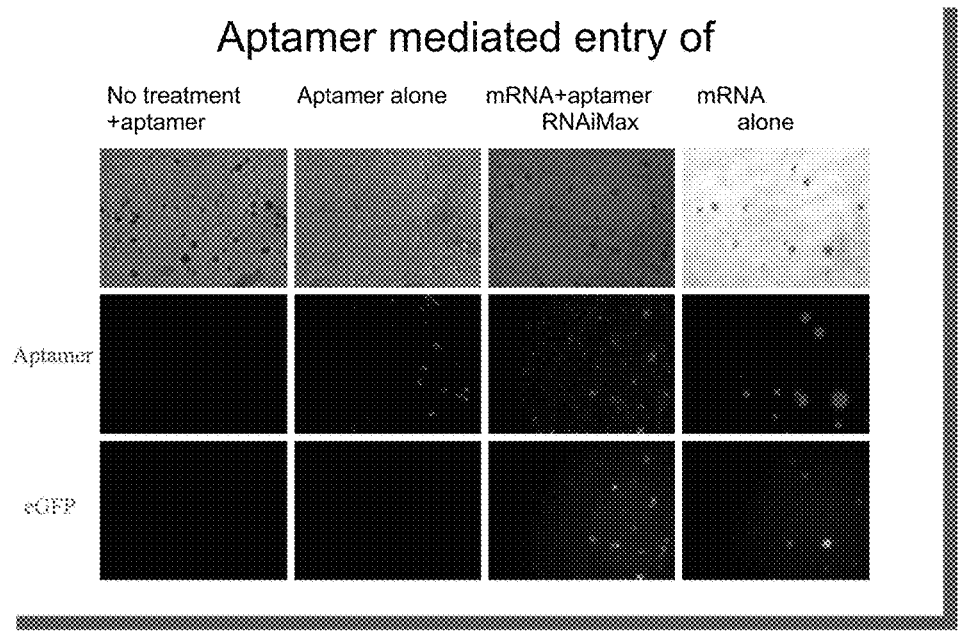
FIG. 21 is a series of images illustrating aptamer mediated entry of mRNA.
Figure 22:
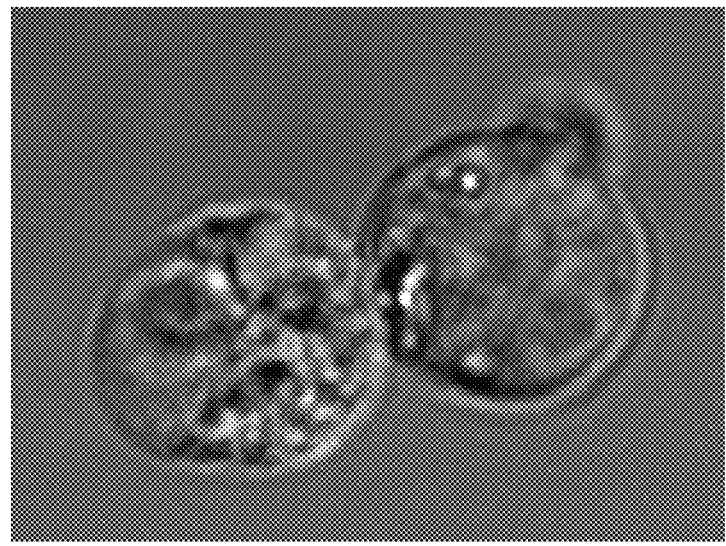
FIG. 22 illustrates that eGFP protein is expressed by Z138 cells after delivery of eGFP mRNA dimerized to BAFF-R1 aptamer (BAFF-R1 aptamer-eGFP mRNA conjugate) 24 hours after addition of the conjugate.

An aptamer labeled with Cy3 was attached to eGFP modified mRNA. The aptamer+mRNA was then delivered to Z138 B cell lymphoma cell line. Cy3 presence at cells suggests aptamer binding (FIGS. 21 and 22). Expression of eGFP in cells suggests that the aptamer mediated mRNA entry and expression.

Discussion of Results

The eGFP mRNA was successfully delivered by aptamer and expressed in BAFF-R present cells. Further, the backbone and base modified eGFP mRNA were successfully synthesized. Transfection of the mRNA via lipofection demonstrated that it was functionally expressed in HEK293 cells.

The next step was to dimerize the in vitro transcribed BAFF-R specific R-1 aptamer with the in vitro transcribed mRNAs using the complementary stick sequence. The dimers formed remained capable of binding purified BAFF receptor in vitro.

The eGFP mRNA was successfully delivered and expressed by Z138 cells. After binding was confirmed, Cy3 labeled aptamer was dimerized to eGFP mRNA and incubated with cells. Expression of eGFP occurred demonstrating aptamer mediated delivery of the mRNA. As described above, other mRNAs may also be conjugated to the aptamer for cell-type specific delivery. For example, delivery of a BAFF-R aptamer for delivery a modified mRNA that triggers death of a B cell lymphoma may be provided.

The stability of the mRNA may need to be increased for in vivo applications. To solve this, 2' FI modifications may be made in addition to other modifications. Development of this delivery approach may lead to new therapeutics.

REFERENCES

The references, patents and published patent applications listed below, and all references cited in the specification above are hereby incorporated by reference in their entirety, as if fully set forth herein.

1. Richman, D. D., et al., *The challenge of finding a cure for HIV infection.* Science, 2009. 323(5919): p. 1304-7.
2. Hutter, G., et al., *Long-term control of HIV by CCR5 Delta32/Delta32 stem-cell transplantation.* N Engl J Med, 2009. 360(7): p. 692-8.
3. Li, M J., et al., *Long-term inhibition of HIV-I infection in primary hematopoietic cells by lentiviral vector delivery of a triple combination of anti-HIV shRNA, anti-CCR5 ribozyme, and a nucleolar localizing TAR decoy.* Mol Ther, 2005. 12(5): p. 900-9.
4. Robbins, M. A., et al., *Stable expression of shRNAs in human CD34+ progenitor cells can avoid induction of interferon responses to siRNAs in vitro.* Nat Biotechnol, 2006. 24(5): p. 566-71.
5. Holt, N., et al., *Human hematopoietic stem/progenitor cells modified by zinc-finger nucleases targeted to CCR5 control HIV-I in vivo.* Nat Biotechnol, 2010. 28(8): p. 839-47.
6. Kim, R. J., et al., *Targeted genome editing in human cells with zinc finger nucleases constructed via modular assembly.* Genome Res, IDD9. 19(}}: p. 1279-88.
7. Nazari, R. and S. Joshi, *CCR5 as target for HIV-I gene therapy.* Curr Gene Ther, 2008. 8(4): p. 264-72.
8. Perez, E. B., et al., *Establishment of HIV-I resistance in CD4+ T cells by genome editing using zinc finger nucleases.* Nat Biotechnol, 2008. 26(7): p. 808-16.
9. Rossi, J J., C. R. June, and D. B. Kohn, *Genetic therapies against HIV.* Nat Biotechnol, 2007. 25(12): p. 1444-54.
10. Umov, F. D., et al., *Genome editing with engineered zinc finger nucleases.* Nat Rev Genet, 2010, 11(9): p. 636-46.
11. Ellington, A. D. and J. W. Szostak, *In vitro selection of RNA molecules that bind specific ligands.* Nature, 1990. 346(6287): p. 818-22.
12. Tuerk, C. and L. Gold, *Systematic evolution of ligands by exponential enrichment.' RNA ligands to bacteriophage T4 DNA polymerase.* Science, 1990. 249(4968): p. 505-10.
13. Chu, T. C., et al., *Aptamer:toxin conjugates that specifically target prostate tumor cells,* Cancer Res, 2006. 66(12): p. 5989-92.
14. Mayer, G., *The chemical biology of aptamers.* Angew Chern Int Ed Engl, 2009. 48(15): p. 2672-89.
15. Zhou, J. and JJ. Rossi, *Bivalent aptamers deliver the punch.* Chern Biol, 2008. 15(7): p. 644-5.
16. Zhou, J, et al., *Selection, characterization and application of new RNA HIV gp 120 aptamers for facile delivery of Dicer substrate siRNAs into HIV infected cells.* Nucleic Acids Res, 2009. 37(9): p. 3094-109.
17. Berges, B. K., et al., *Mucosal transmission of R5 and X4 tropic HIV-I via vaginal and rectal routes in humanized Rag2-1-gammac-1-(RAG-hu) mice.* Virology, 2008. 373 (2): p. 342-51.
18. Denton, P. W. and IV. Garcia, *Novel humanized murine models for HIV research.* Curr HIV/AIDS Rep, 2009. 6(1): p. 13-9.
19. Kumar, P., et al., *T cell-specific siRNA delivery suppresses HIV-I infection in humanized mice.* Cell, 2008. 134(4): p. 577-86.
20. Legrand, N., et al., *Humanized mice for modeling human infectious disease.' challenges, progress, and outlook.* Cell Host Microbe, 2009. 6(1): p. 5-9.'

21. Van Duyne, R., et al., *The utilization of humanized mouse models for the study of human retro viral infections.* Retrovirology, 2009. 6: p. 76
22. Berges, B!K., et al., *HIV-I infection and CD4 T cell depletion in the humanized Rag2-I-gamma c-I(RAG-hu) mouse model.* Retrovirology, 2006. 3: p. 76.
23. Berges, B K., et al., *Humanized Rag2(-I-)gammac(-I-) (RAG-hu) mice can sustain long-term chronic HIV-I infection lasting more than a year.* Virology, 2010. 397 (1): p. 100-3.
24. Moir, S. and A. S. Fauci, *B cells in HIV infection and disease.* Nat Rev Inununol, 2009. 9(4); p. 235-45.'
25. Xue, Y. N., et al., *Improving gene delivery efficiency of bioreducible poly(amidoamine)s via grafting with dendritic poly(amidoamine)s.* Macromol Biosci, 2010. 10(4): p. 404-14.'
26. Khaled, A., et al., *Controllable self-assembly of nanoparticles for specific delivery of multiple, therapeutic molecules to cancer cells using RNA nanotechnology.* Nano Lett, 2005. 5(9): p. 1797-808.
27. Song, R. I., et al., *Molecularly cloned SHIV-II 57ipd3N4: a highly replication-competent, mucosally transmissible R5 simian-human immunodeficiency virus encoding HIV clade C Env.* J Virol, 2006. 80(17); p. 8729-38.
28. Zhou, 1., et al., *Novel dual inhibitory function aptamer-siRNA delivery system for HIV-I therapy.* Mol Ther, 2008. 16(8): p. 1481-9.
29. Kiem, H. P., et al., *Foamy combinatorial anti-HIV vectors with MGMTP140K potently inhibit HIV-I and SHIV replication and mediate selection in vivo.* Gene Ther, 2010. 17(1): p. 37-49.
30. Tro bridge, G p., et al, *Protection of stem-cell-dedved lymphocytes in a primate AIDS gene. Therapy model after in vivo selection.* PLoS One, 2009. 4(11): p. e7693."-
31. Warren, 1., et al., *Highly Efficient Reprogramming to Pluripotency and Directed Differentiation of Human Cells with Synthetic Modified mRNA.* Cell Stem Cell, 2010.
32. Wu, J., et al., *Polycationic dendrimers interact with RNA molecules: polyamine-dendrimers inhibit the catalytic activity of Candida ribozymes.* Chern Commun (Camb), 2005(3): p. 313-5.
33. Zhou, J., et al., *PAMAM dendrimers for efficient siRNA delivery and potent gene silencing.* Chern Commun (Camb), 2006(22): p. 2362-4.
34. J. S. Thompson et al., *Science* 293, 2108 (Sep. 14, 2001)
35. L. Warren et al., *Cell Stem Cell* 7, 618 (November 5).
36. K. Kariko et al., *Mol Ther* 16, 1833 (November, 2008).

What is claimed is:

1. An imaging method comprising:
   administering an effective dose of one or more aptamer-mRNA conjugates to a subject, wherein each of the one or more aptamer-mRNA conjugates comprises:
      an aptamer component that binds a membrane associated protein on a target cell; and
      an mRNA molecule that encodes a diagnostic agent that is expressed by the target cell, wherein the aptamer component is conjugated to the mRNA molecule; and
   exposing the subject to an imaging method.

2. The imaging method of claim 1, wherein the diagnostic agent that is expressed by the target cell is a fluorescent protein or peptide.

3. The imaging method of claim 2, wherein the fluorescent protein or peptide is green fluorescent protein (GFP), enhanced GFP (eGFP), red fluorescent protein, blue fluorescent protein, yellow fluorescent protein, cyan fluorescent protein, sapphire fluorescent protein, reef coral fluorescent protein, or a derivative thereof.

4. The imaging method of claim 1, wherein the diagnostic agent that is expressed by the target cell is a luminescent protein or peptide.

5. The imaging method of claim 4, wherein the luminescent protein or peptide is luciferase, aequorin, or a derivative thereof.

6. The imaging method of claim 1, wherein the aptamer binds a target molecule on the surface of a cell and the mRNA molecule is expressed in the cell and visualized by the imaging method.

7. The imaging method of claim 1, wherein the aptamer binds a target molecule on a pathogen and visualized by the imaging method.

8. The imaging method of claim 7, wherein the pathogen is human immunodeficiency virus (HIV).

9. The imaging method of claim 1, wherein the imaging method is positron emission tomography (PET), computer assisted tomography (CAT), single photon emission computerized tomography, x-ray, fluoroscopy, or magnetic resonance imaging (MRI).

10. The imaging method of claim 1, wherein the aptamer-mRNA conjugates are delivered via dendrimers.

11. The imaging method of claim 1, wherein the aptamer component and the mRNA molecule are conjugated covalently.

12. The imaging method of claim 1, wherein the aptamer component and the mRNA molecule are conjugated non-covalently.

* * * * *

UNITED STATES PATENT AND TRADEMARK OFFICE
CERTIFICATE OF CORRECTION

| | | |
|---|---|---|
| PATENT NO. | : 10,272,165 B2 | Page 1 of 1 |
| APPLICATION NO. | : 15/207280 | |
| DATED | : April 30, 2019 | |
| INVENTOR(S) | : John J. Rossi et al. | |

It is certified that error appears in the above-identified patent and that said Letters Patent is hereby corrected as shown below:

In the Specification

Statement of Government Interest section, Column 1, Lines 19-22, please delete:
"The present invention was made with government support under Grant Nos. AI29329, AI42552 and HL07470 awarded by the National Institutes of Health. The Government has certain rights in the invention."

And insert:
--This invention was made with government support under HL074704, AI029329, and AI042552 awarded by the National Institutes of Health. The government has certain rights in the invention.--

Signed and Sealed this
Sixteenth Day of April, 2024

Katherine Kelly Vidal
*Director of the United States Patent and Trademark Office*